United States Patent [19]

Saravia et al.

[11] Patent Number: 5,484,402
[45] Date of Patent: Jan. 16, 1996

[54] SURGICAL SUCTION IRRIGATOR

[75] Inventors: Heber Saravia, San Francisco; Christopher S. Jones, Palo Alto; Charles L. Nelson, Pleasanton, all of Calif.

[73] Assignee: Stryker Corporation, Kalamazoo, Mich.

[21] Appl. No.: 176,130

[22] Filed: Dec. 30, 1993

[51] Int. Cl.$^6$ .............................. A61M 1/00; A61M 5/00
[52] U.S. Cl. .................. 604/35; 604/249; 604/33
[58] Field of Search ................... 604/27–36, 39, 604/151, 246, 249, 250, 408, 411, 414; 433/84, 85

[56] References Cited

U.S. PATENT DOCUMENTS

| | | |
|---|---|---|
| 3,861,383 | 1/1975 | Kovach . |
| 4,493,694 | 1/1985 | Wuchinich ................................. 604/35 |
| 4,935,005 | 6/1990 | Haines ...................................... 604/35 |
| 4,982,739 | 1/1991 | Hemstreet et al. . |
| 5,120,305 | 6/1992 | Boehringer et al. ..................... 604/35 |
| 5,142,723 | 9/1992 | Lustig et al. . |
| 5,170,779 | 12/1992 | Ginsberg . |
| 5,186,714 | 2/1993 | Boudreault et al. ..................... 604/35 |
| 5,197,460 | 3/1993 | Ito et al. . |
| 5,203,769 | 4/1993 | Clement et al. ......................... 604/35 |
| 5,224,929 | 7/1993 | Remiszewski ........................... 604/35 |
| 5,295,956 | 3/1994 | Bales et al. .............................. 604/35 |
| 5,322,503 | 6/1994 | Desai ...................................... 604/35 |

FOREIGN PATENT DOCUMENTS 0021388  12/1992  WIPO ................................. 604/151

Primary Examiner—C. Fred Rosenbaum
Assistant Examiner—Frank Wilkens, III
Attorney, Agent, or Firm—Flynn, Thiel, Boutell & Tanis

[57] ABSTRACT

A surgical irrigation system is suitable for endoscopic and other surgical procedures. A hand held handpiece has a forward protruding hollow tip for supplying irrigation liquid to a surgical site, a hand actuable control for controlling irrigation liquid flow to the tip, and an irrigation liquid inlet. A self contained pumping unit is locatable adjacent a source of irrigation liquid and remote from the handpiece. The pumping unit comprises a housing containing an outlet for irrigation liquid, a pumping member for pumping irrigation liquid through the outlet, a motor for driving the pumping member, and an electric battery assembly for energizing the motor. An elongate tube connects the pumping outlet to the handpiece irrigation liquid inlet for supplying pumped irrigation liquid to the handpiece.

18 Claims, 39 Drawing Sheets

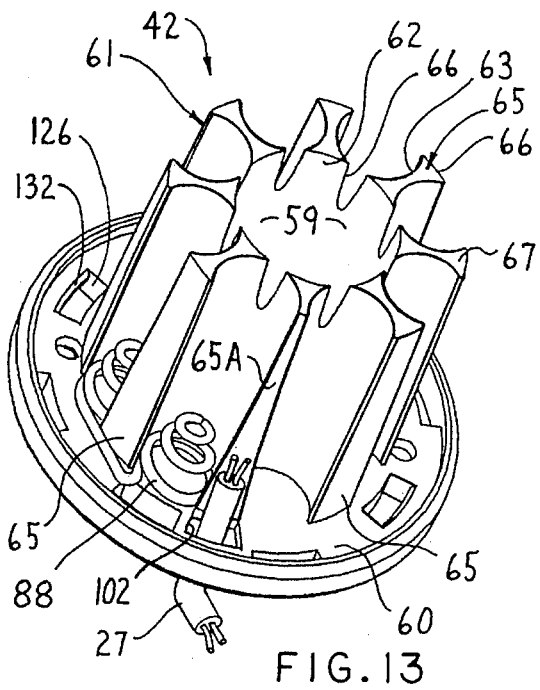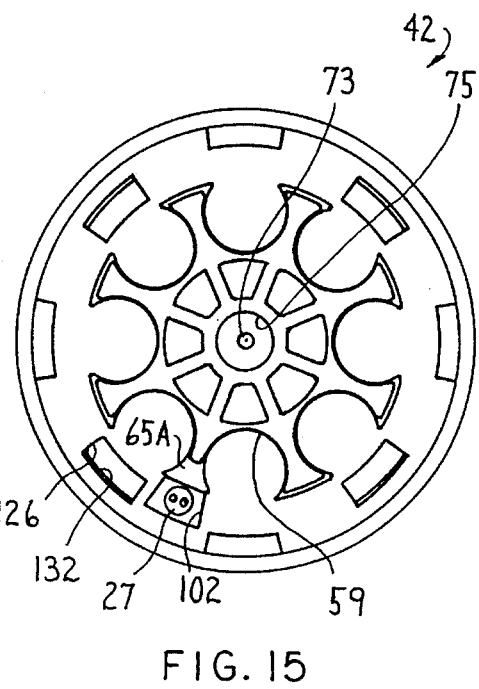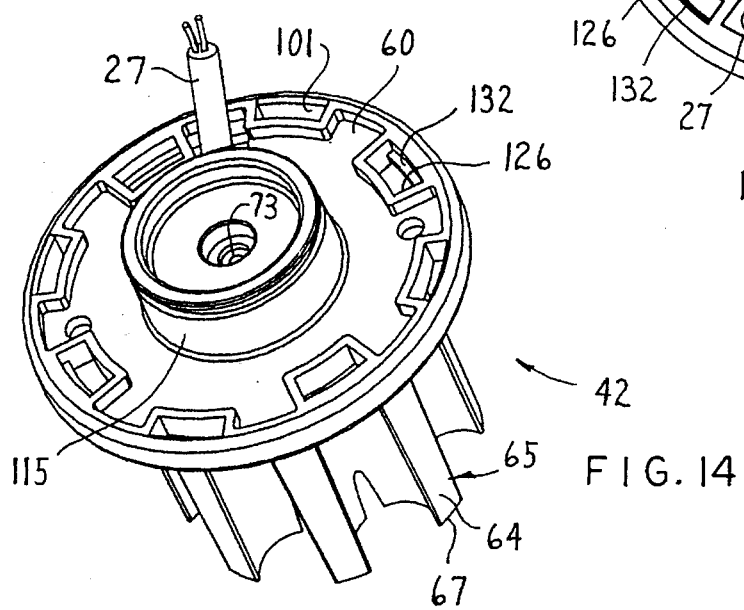

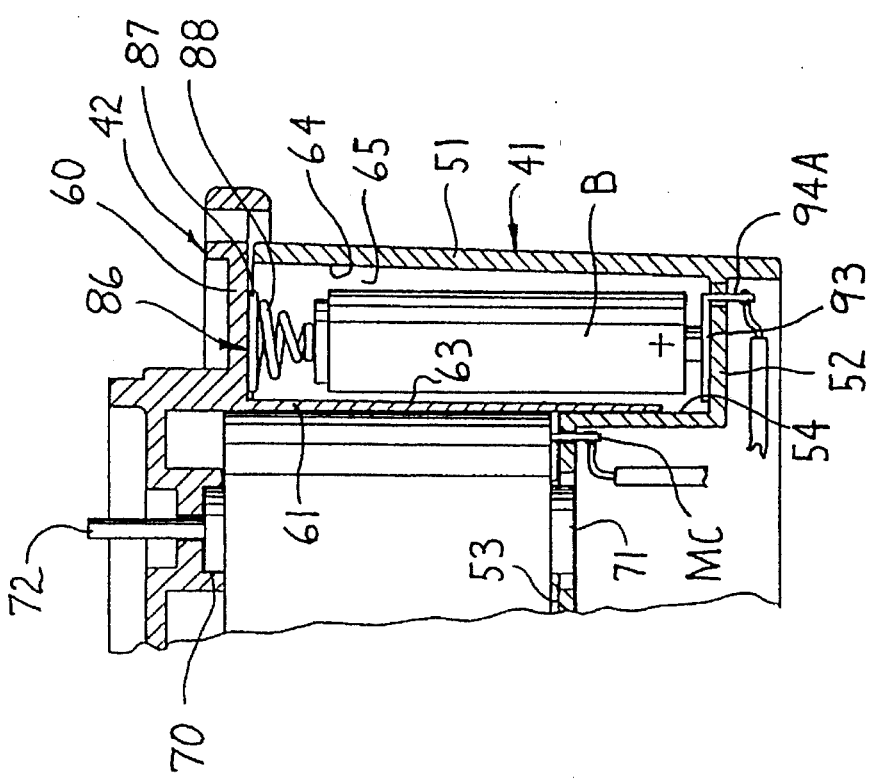
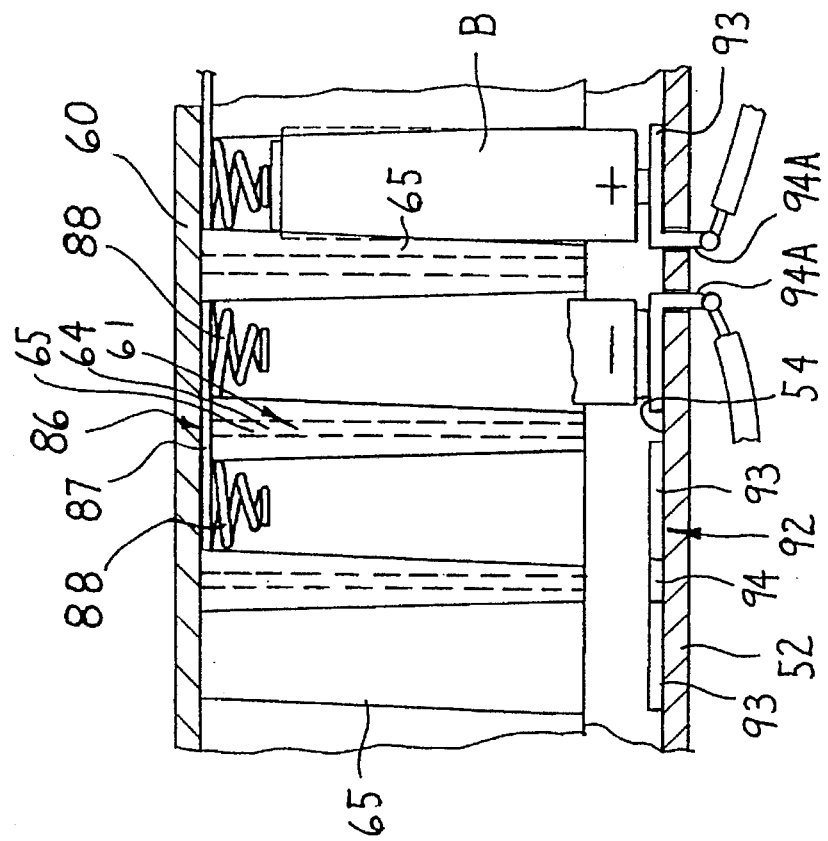

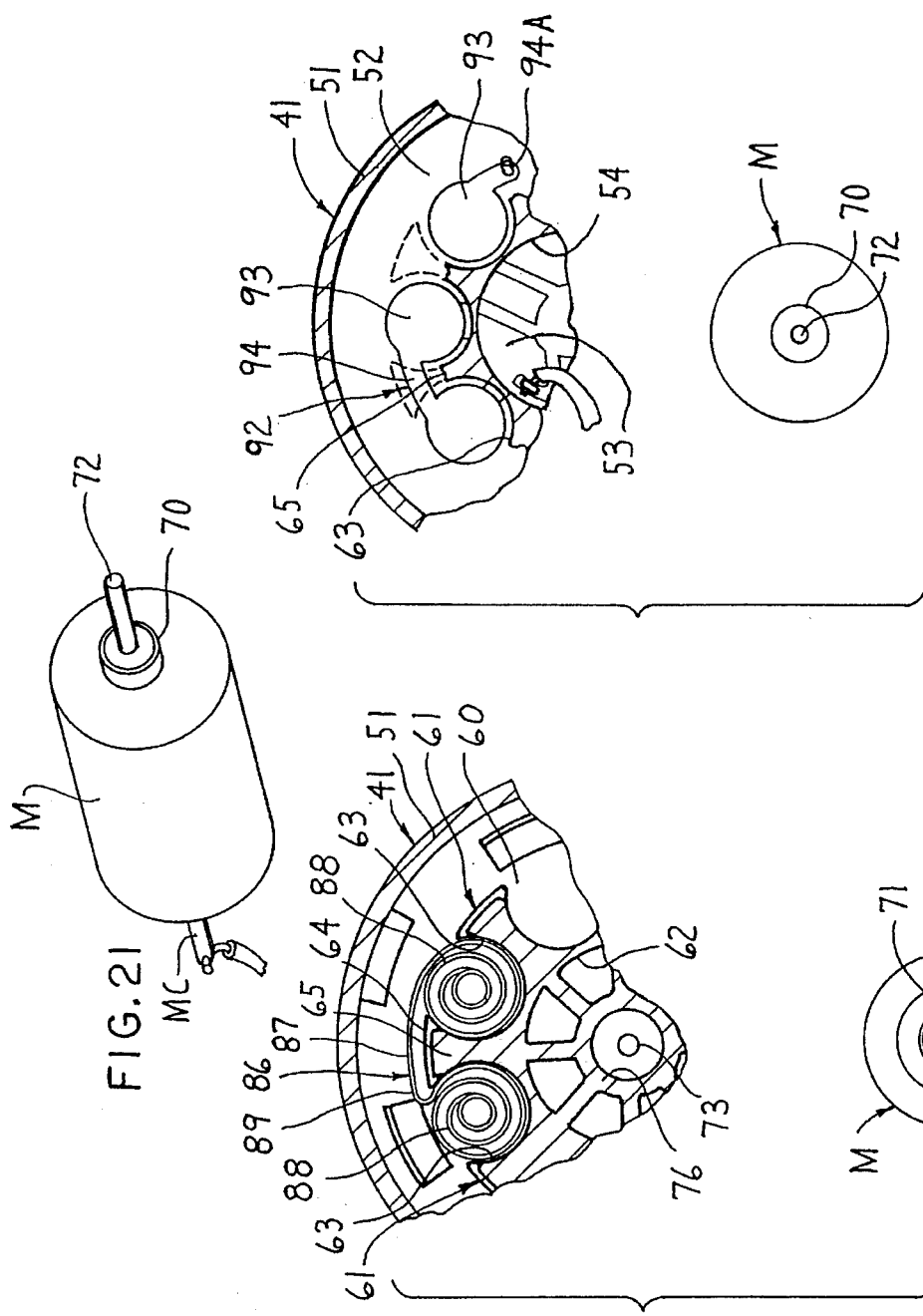

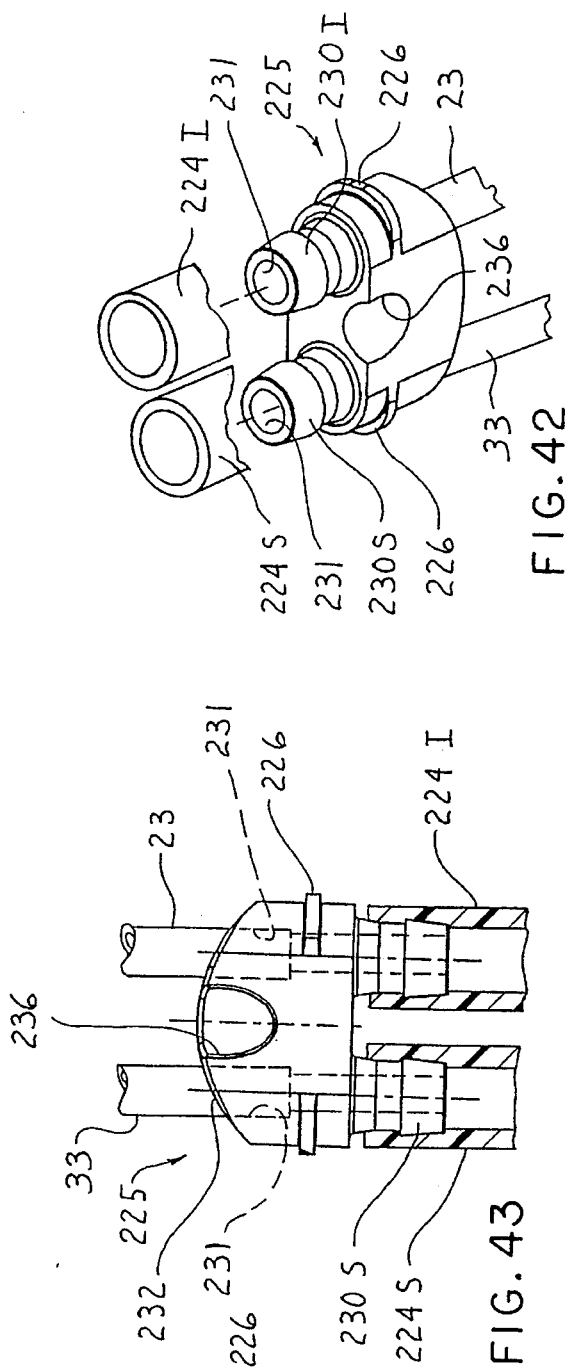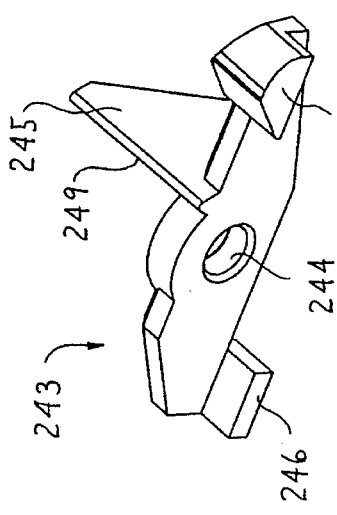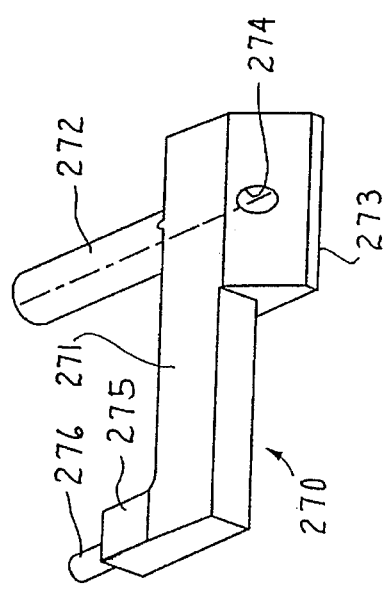

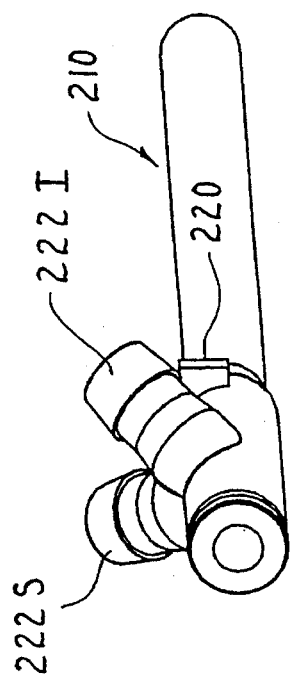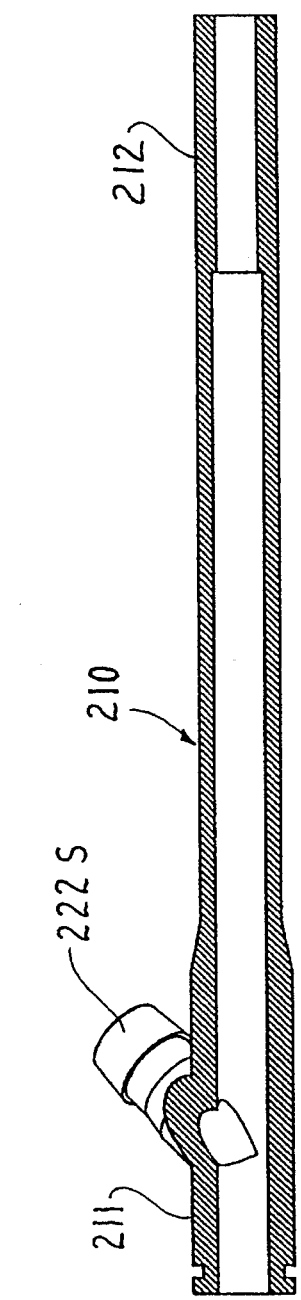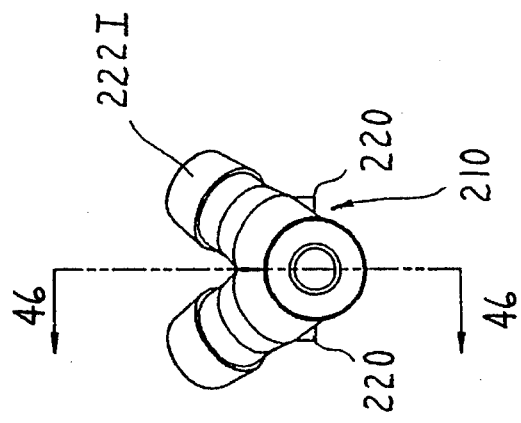

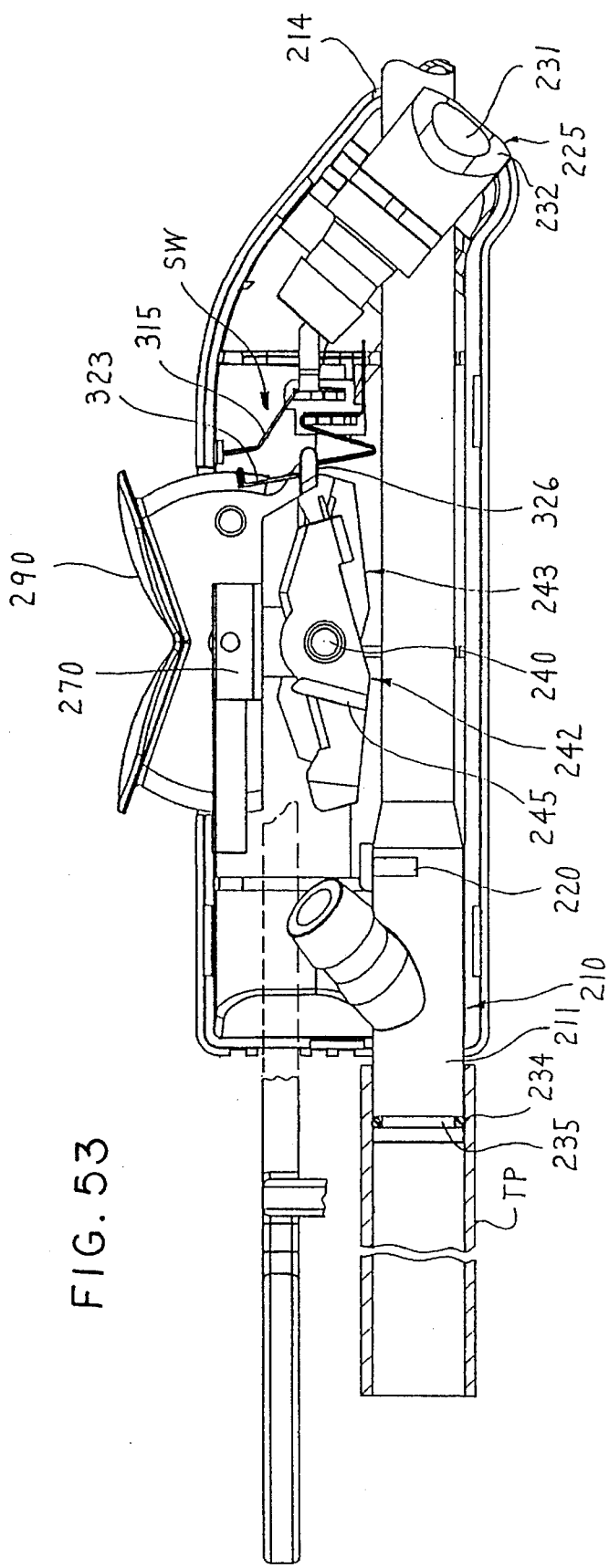
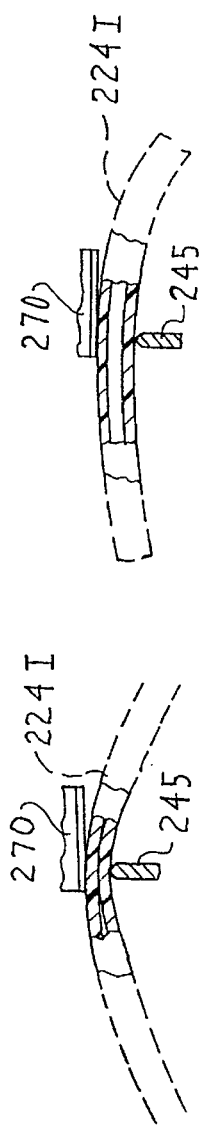
FIG. 53
FIG. 53A
FIG. 53B

SURGICAL SUCTION IRRIGATOR

FIELD OF THE INVENTION

This invention relates to a surgical suction and irrigation system, and more particularly to one adaptable for use in endoscopic surgery.

BACKGROUND OF THE INVENTION

Stryker Corporation, the assignee of the present invention, filed, Apr. 19, 1993, U.S. patent application Ser. No. 08/049 144 (attorney's reference Stryker Case 130) disclosing a suction irrigation system in which a handpiece is supplied with irrigation liquid, through an elongate flexible tube, from a remote source. The system includes an electric motor drive pump powered by a battery pack and controlled by an electric switch. The electric switch is on the handpiece and the battery pack is fixed along the irrigation liquid tube between the handpiece and irrigation liquid source, at a point remote from the handpiece. An electric cable extends between the battery pack and handpiece and along the irrigation liquid tube. Such system is marketed under the trademark SURGILAV PLUS (TM).

However, the SURGILAV PLUS (TM) system, while adaptable to a variety of surgical uses, was not specifically directed toward endoscopic surgery. Moreover, it differs structurally and operationally in a number of respects from the present invention.

A number of other companies market irrigation and suction irrigation systems. However, the present inventors have not found same to be entirely satisfactory for their purposes.

Therefore, in a continuing effort to improve on surgical suction irrigation systems, particularly endoscopic suction irrigation systems, the present invention has been developed.

Further objects and purposes of the present invention will be apparent to persons acquainted with apparatus of this general kind, upon reading the following description and inspecting the accompanying drawings.

SUMMARY OF THE INVENTION

A surgical irrigation system is suitable for endoscopic and other surgical procedures. A hand held handpiece has a forward protruding hollow tip for supplying irrigation liquid to a surgical site, a hand actuable control for controlling irrigation liquid flow to the tip, and an irrigation liquid inlet. A self contained pumping unit is locatable adjacent a source of irrigation liquid and remote from the handpiece. The pumping unit comprises a housing containing an outlet for irrigation liquid, a pumping member for pumping irrigation liquid through the outlet, a motor for driving the pumping member, and an electric battery assembly for energizing the motor. An elongate tube connects the pumping outlet to the handpiece irrigation liquid inlet for supplying pumped irrigation liquid to the handpiece.

BRIEF DESCRIPTION OF THE DRAWINGS

FIGS. 13 and 14 are pictorial views of the locator of FIGS. 2–4, looking respectively toward the bottom and top thereof.

FIG. 15 is a bottom view of the FIG. 13 locator.

FIG. 17 is a fragmentary generally schematic view illustrating a location of battery contacting elements in the FIG. 13 locator.

FIG. 18 is a somewhat schematic fragment of FIG. 6 showing location of the motor and battery in the locator of FIG. 13.

FIG. 19 is a fragmentary, somewhat schematic, sectional view generally as taken on the line 19—19 of FIG. 6 and showing a lower battery contact.

FIG. 20 is a fragmentary, somewhat schematic, sectional view generally as taken on the line 20—20 of FIG. 6 and showing an upper battery contact.

FIG. 21 is a pictorial view of the motor of FIG. 19.

FIG. 39 is an enlarged pictorial view of the irrigation anvil of FIG. 29.

FIGS. 40 and 41 are pictorial views of the suction and irrigation pinch levers, respectively, of FIG. 29.

FIG. 42 is a pictorial view, taken substantially from the front, of the adapter block of FIG. 32.

FIG. 43 is a plan view taken from above and behind of the FIG. 42 adapter block.

FIG. 44 is a pictorial view of the conduit of FIG. 29.

FIG. 45 is a front view of the FIG. 44 conduit.

FIG. 46 is a central cross-sectional view of the FIG. 44 conduit.

FIG. 53 is an elevational view of the handpiece above-referenced, taken from the irrigation side, with the guard pin in place but with the rear portion of the guard pin shown only in dotted line to better show internal handpiece parts located behind it and with the irrigation side half shell removed.

FIGS. 53A and 53B are fragments of FIG. 53 with the irrigation hose added and shown in its closed and opened positions respectively.

FIGS. 56A and 56B are fragments of FIG. 56 with the suction tube added and shown in its closed and opened positions respectively.

DETAILED DESCRIPTION

Figure 3:
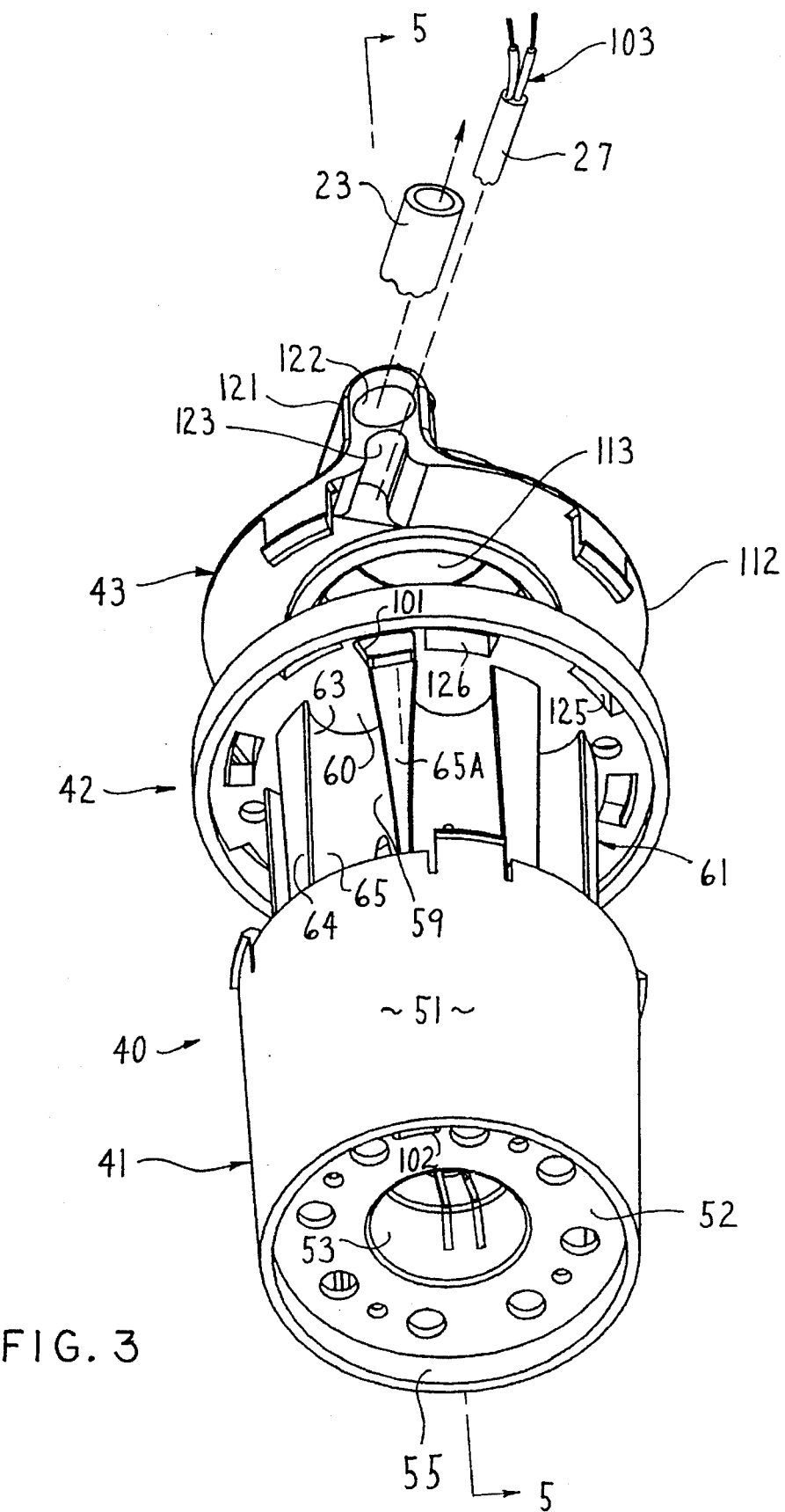

The suction irrigation system 10 (FIG. 1) embodying the invention comprises a pressure liquid unit 11 having a upstanding liquid inlet connector 12 for direct connection to a liquid outlet connector 13 on a conventional irrigation liquid supply IL. In the example shown in FIG. 1, the irrigation liquid supply IL is a conventional irrigation liquid supply bag 14 and the connector 13 is a conventional luer connector. As here shown, the irrigation liquid bag 14 may be conventionally supported by the usual horizontal arm 15 adjustably fixed on the usual standing pole 16, the arm and pole being, for example, of the kind usually employed to support an IV (intravenous) bottle, irrigation liquid bag, or the like. The pressure liquid unit 11 may be supported from the bag 14 simply by interconnection of the respective connectors 12 and 13. Alternately, additional support means may be employed, such as a strap (not shown) fixed in any convenient way to the outside of the pressure liquid unit 11 and to the arm 15. Alternatively, the pressure liquid unit 11 may be supported by a conventional bracket 18 conventionally clamped at 19 to the pole 16, and encircling the pressure liquid unit 11 snugly, as indicated generally at 20. The pressure liquid unit 11 pressurizes irrigation liquid tube 23 (FIG. 3) which is flexible and runs at length (for example 6–12 feet) to a handpiece 26 to be gripped and controlled by a user, typically a surgeon or surgical assistant. An electric cable 27 is comparable in length to the tube 23 and runs with it from the pressure liquid unit 11 to the handpiece 26. The cable 27 preferably is, for neatness, fixed along the tube 23, for example by longitudinally spaced conventional clips 32 or longitudinal bonding. A flexible suction tube 33 runs from the handpiece 26 to a conventional suction source SS, such as a conventional hospital operating room suction port. The tubes 23 and 33 and cable 27 preferably run to the rear end portion 34 of the handpiece 26. The handpiece 26 in the embodiment shown has a rigid tubular tip TP (hereafter described) releasably extending forward from the front end portion 36 thereof for direction toward a surgical site, either directly or through a conventional endoscopic cannula (a fragment of which is schematically indicated at CA in FIG. 1), for performing irrigation and suction removal of debris at a surgical site SU.

Pressure Liquid Unit 11

Figure 2:
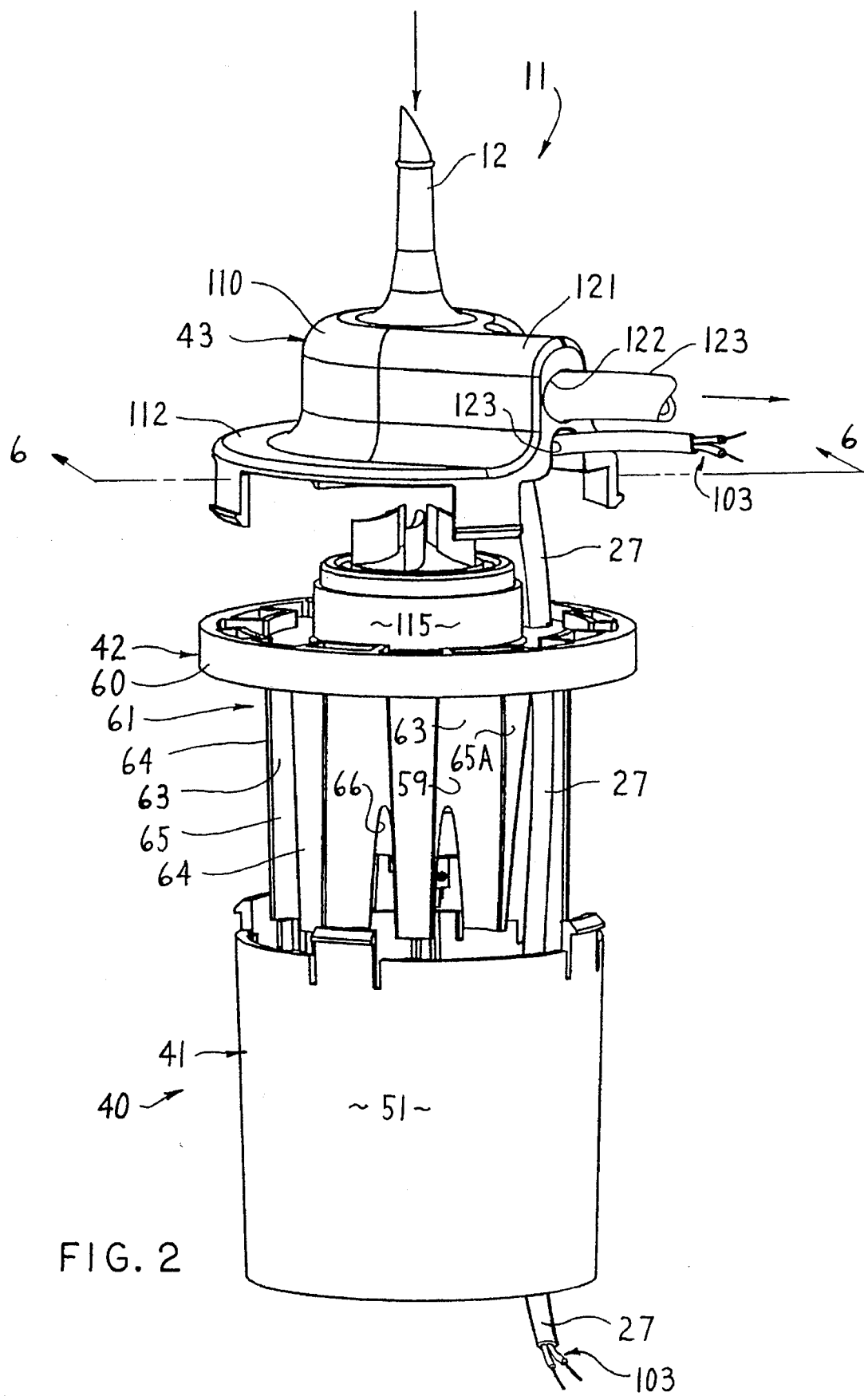
FIGS. 2–4 are exploded pictorial views of the pressure liquid unit of FIG. 1 taken from three different vantage points of differing height and circumferential location.

The pressure liquid unit 11 comprises (FIG. 2) a housing generally indicated at 40, in turn comprising an upward opening cup 41, a motor and battery locator 42 and a pump cover 43.

The cup 41 comprises an open top 50 (FIGS. 7–9), a slightly downward tapered side/wall 51 and a generally closed bottom wall 52. The bottom wall as an upstepped central motor support drum 53. The drum is of circular cross-section. An annular, upward facing, battery receiving groove 54 is defined radially and coaxially between the cup side wall and drum.

Figure 5:
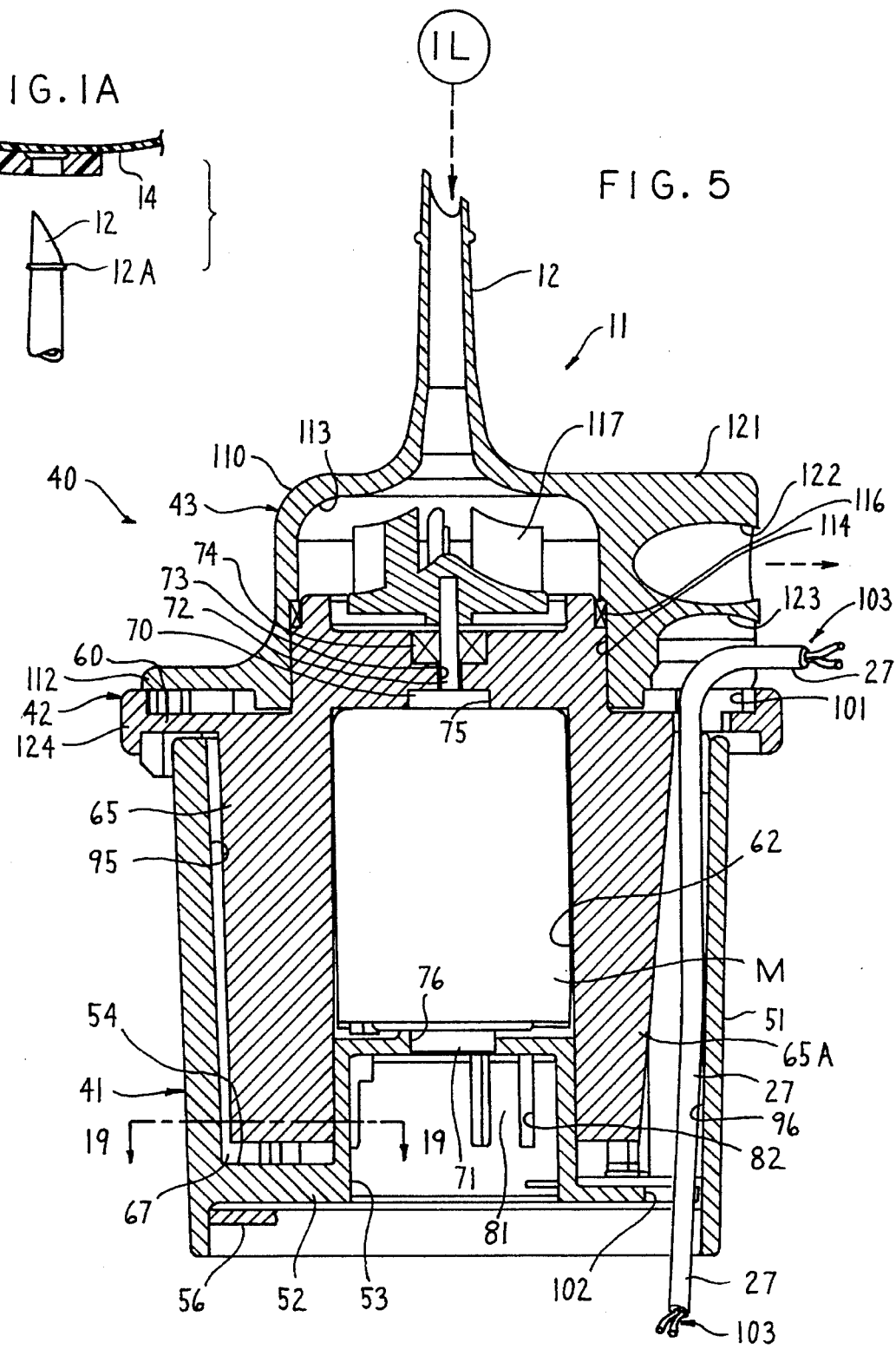
FIG. 5 is a central cross-sectional view of the pressure liquid unit of FIGS. 1–4 taken on a diametral cutting plane running through the cable space and indicated generally by the line 5—5 in FIG. 3.

The battery and motor locator 42 (FIGS. 6 and 13) comprises a deck 60 adapted to seat upon the top edge of the cup side wall 51 and substantially close the open top of the cup 41. A finned column 61 fixedly coaxially depends from the deck 60. The column comprises a hollow tubular wall 59 defining a downward opening recess 62 located coaxially therein and closed at its top by the deck 60. The finned exterior of the column 61 is defined by a plurality (here eight for example) of circular cross-section grooves 63 extending the length of the column. The grooves 63 are circumferentially evenly spaced and circumferentially separated by axial, curved cross-section, ridge-like fins 65 radially outwardly extending from the tubular wall 59. The radially outermost surface 64 of the column is somewhat tapered downward in correspondence to the taper of the sidewall 51 of the cup. The circular cross-section grooves 63 have axes similarly convergent downward toward the central axis of the locator 42 (and thus toward the central axis of the recess 62 and deck 60). The grooves 63 thus have bottom portions which cut into the recess 62 at the arched notches 66. The column 61 is sized to depend snugly into the cup 41, with the deck 60 mounted atop the side wall 51 of the cup. In this installed position, the bottom of the hollow column 61 extends down into the annular groove 54 between the drum and side wall of the cup and the drum 53 is snugly but slidably received upward into the bottom portion of the central recess 62 of the locator. With the locator 42 installed in the cup 41, the fins 65 have their bottom ends 67 (FIGS. 5 and 6) spaced above the bottom wall 52 of the cup 41.

The locator 42 and cup 41, when assembled, are intended to locate therewithin in a circumferential array, plural (here eight) conventional AA batteries B (FIGS. 17 and 18), one in each of the circumferentially distributed grooves 63 of the locator, and a battery powered motor M in the recess 62.

Figure 7:
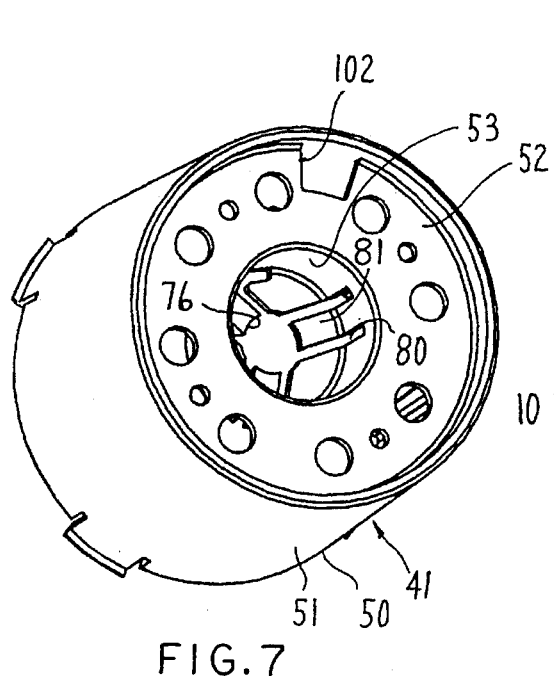
FIGS. 7–9 are pictorial views of the cup of FIGS. 2–6, taken from different viewpoints, to show the bottom of the cup in FIG. 7 and to show different viewpoints of the interior of the cup in FIGS. 8 and 9.
Figure 8:
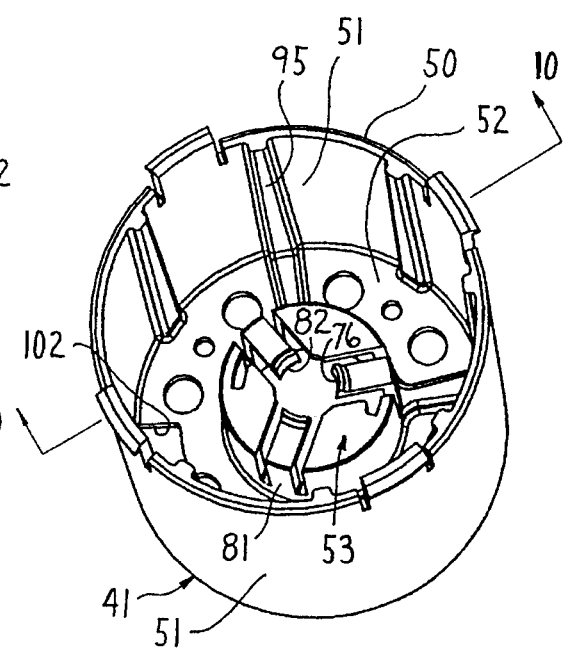
Figure 9:
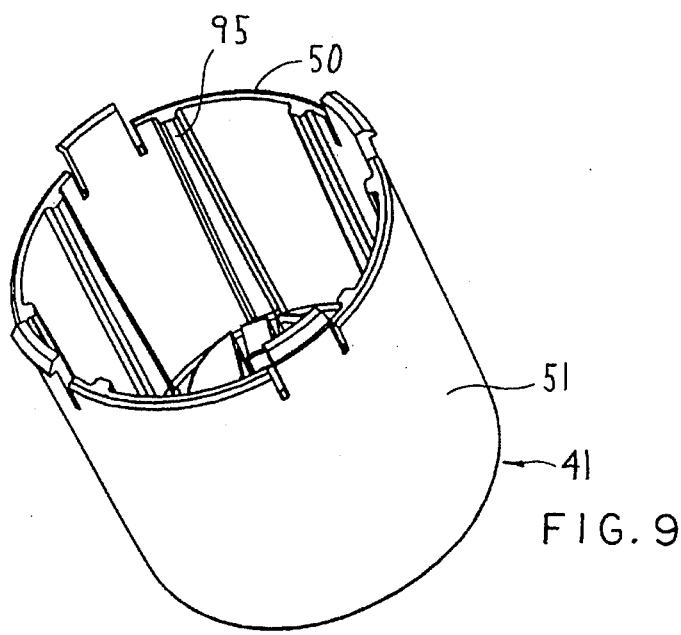

The motor M is, in the embodiment shown, shaped generally as a right circular cylinder with coaxially protruding top and bottom bosses 70 and 71. A shaft 72 extends coaxially up through the top boss 70 and is rotatable with respect thereto. See particularly FIGS. 5 and 21. The motor M is snugly but slidably received up into the recess 62 of the locator 42 with its shaft 72 extending up through a coaxial hole 73 in the deck 60. A conventional annular seal 74 (FIG. 5) recessed in the top of the deck 60, admits the shaft 72 rotatably upwardly therethrough but prevents liquid leakage therepast downward along the shaft toward the top of boss 70. The motor M is coaxially located in the recess 62 by snug reception of its top boss 70 in a down facing central recess 75 in the deck 60, and its bottom boss 71 in a central opening 76 in the top of the drum 53 (FIGS. 7 and 8).

Figure 10:
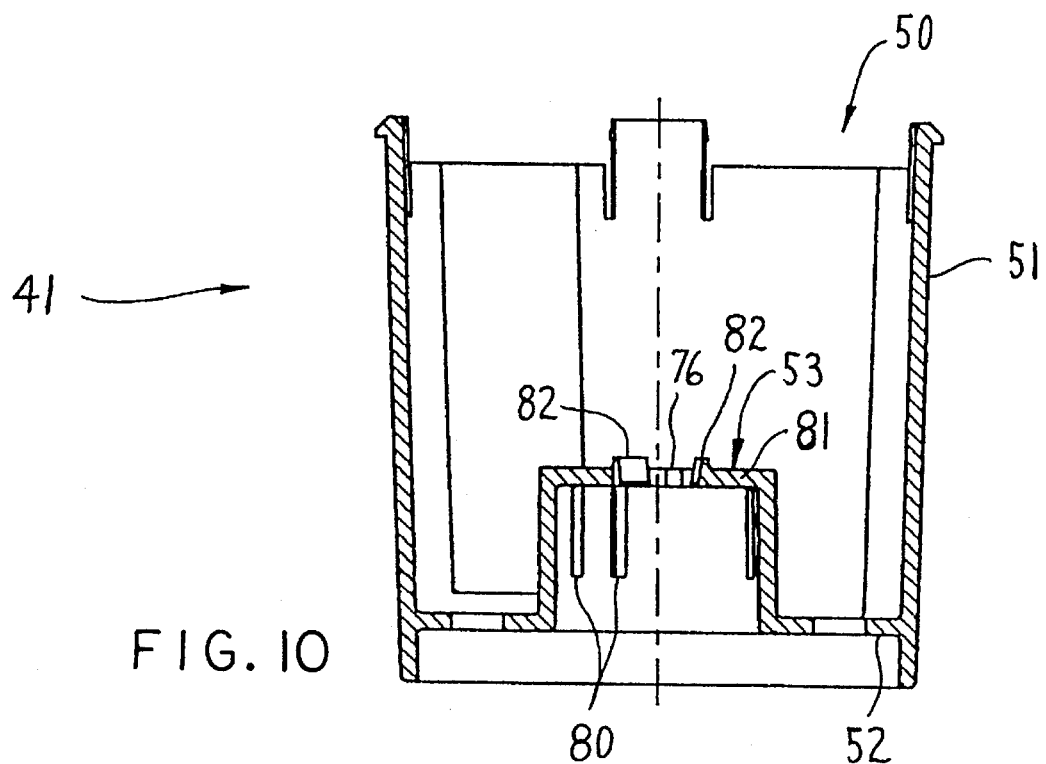
FIG. 10 is a central cross-sectional view of the cup, substantially as taken on the line 10—10 of FIG. 8.

The top and sides of the drum 53 are cut by three evenly circumferentially spaced pairs of parallel slots 80 communicating with the central opening 76. The parallel slots 80 of each pair define therebetween a generally L-shaped segment 81 of the drum top and side walls. The upper and radially inner ends of the three segments 81 are enlarged in cross-section to define corresponding circumferentially spaced rim parts 82 which together define the central opening 76 through the top of the drum. As seen in FIG. 10, the rim parts 82 are slightly wedge-shaped, to converge downwardly slightly and thereby tend to center therebetween, in wedging fashion, the bottom boss 71 of the motor M. The L-shaped segments 81, being separated from the rest of the drum 53 by the flanking slots 80, can resiliently deflect, in the manner of a leaf spring, to snugly grip the bottom boss 71 of the motor M and thereby firmly and fixedly center the motor M coaxially with respect to the cup 41 and locator 42.

Electrically conductive spring wire, upper contacts 86 (FIGS. 16, 17, 18 and 20) each comprise a generally straight bight flanked by integral coil compression spring portions 88 of frustoconical profile. The profile of each coil spring portions 88 tapers downwardly as seen in FIGS. 17 and 18. The bight 87 and widened base of each spring portion 88 is backed by the underside of the deck 60. The coil spring portions 88 each are snugly frictionally gripped by the surrounding fins 65 to firmly hold each upper contact 86 axially against the underside of the deck 60. The upper contacts 86 are easily installed on the column 61 by placing same in registry with the bottom end 67 (FIG. 14) of the corresponding fin 65 and then sliding same there along upwardly into contact with the underside of the deck 60.

Conductive, flat plate, lower contacts 92 (FIGS. 16–19) each comprise a pair of circumferentially spaced circular disks 93 connected by an integral circumferentially extending strap 94. In one of the lower contacts 92, the strap 94 is cut in the middle to form respective terminal tabs 94A (FIGS. 17 and 19) for connection of the batteries B, in circuit with the motor M and a switch SW hereafter described. The disks 93 are respectively fixedly located coaxially with the grooves 63 of the column 61 but are spaced below the column 61 to lie fixedly atop the bottom wall 52 of the cup 41, within the annular groove 54 thereof. The disks 93 are fixed atop the cup bottom wall 52 by any convenient means.

Figure 12:
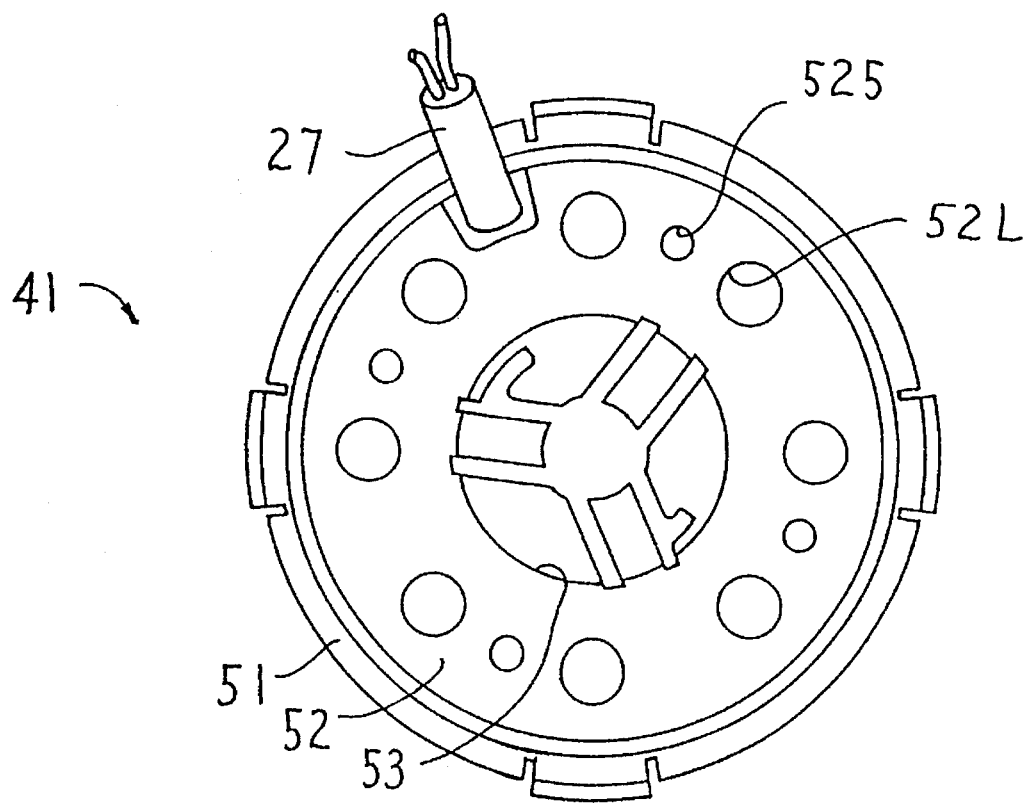
FIG. 12 is a bottom view of the FIG. 10 cup.

In one unit constructed according to the present invention, the lower contacts 92 were installed in a particularly advantageous manner while producing the cup 41 by injection molding. As seen in FIG. 12, the bottom wall 52 of the cup 51 is perforated by circumferentially spaced large and small holes 52L and 52S respectively. Same are left by wide and narrow mold pins (not shown) upstanding from a (not shown) mold floor underlying the bottom wall 52 (FIG. 10) of the cup 41 when forming same by molding. Eight of the conductive circular disks 93 (FIG. 19) were continuously connected in a circle by the straps 94 and supported just above the mold floor by the wide mold pins which produce the larger diameter holes 52L abovementioned. Plastic material injected into the mold filled the area between the disks 93 and mold bottom to form the cup bottom wall 52 against the underside of the disks 93. Insertion of a tool up through the small holes 52S break the straps 94 located thereabove to leave four pairs of disks 93 unconnected by straps, with a strap 94 between the disks 93 of each pair, as in FIGS. 16 and 19.

In the embodiment shown, the motor M requires a nominal 12-volt DC power supply. Accordingly, it is appropriate to provide eight batteries B of the nominal 1 ½ volt inexpensive, commercially available AA type. In view of their long shelf life and relatively high power storage capability and capability to supply adequate voltage until nearly fully discharged, alkaline batteries are preferred.

Figure 11:
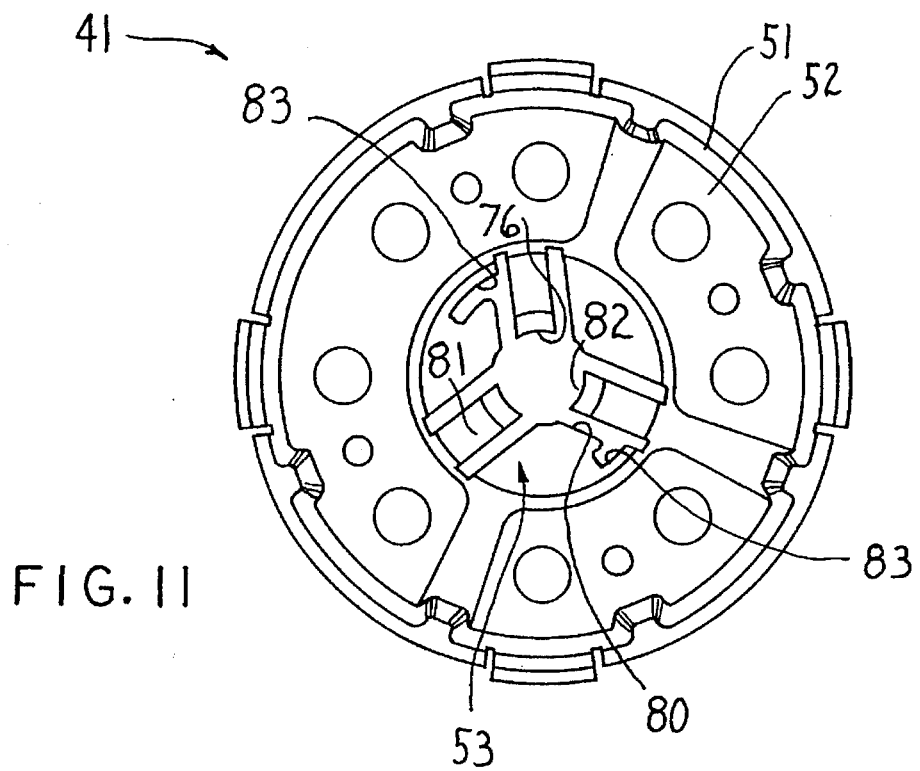
FIG. 11 is a top view of the FIG. 10 cup.

In the embodiment shown, the motor M has a pair of electrical contacts MC protruding from the bottom thereof and electrically energizable for rotating the motor shaft. In the embodiment shown in FIG. 11, circumferential extensions 83 of the slots 80 are diametrically opposed in the top of the drum 53 and the electric contacts MC of motor M extend downwardly therethrough for electrical connection in circuit with the batteries B and the switch SW hereafter described.

Circumferentially spaced ribs 95 (FIG. 8) extend upward along and protrude radially in on the sidewall 51 of the cup 41 and closely radially oppose corresponding ones of the fins 65 of the locator 42. However, the radially outer part of the one of the fins 65 is eliminated, as indicated at 65A in FIG. 13, and its corresponding upstanding cup rib 95 is eliminated, leaving a cable space 96 radially therebetween. Electric cable 27 (FIG. 5) extends through this cable space 96, substantially vertically along the cup sidewall 51 and exits up through a cable port 101 in the deck 60 near the edge thereof and down through a cable port 102 in the bottom wall 52 of the cup 41. The electric cable 27 here incorporates two insulated electric wires generally indicated at 103.

Figure 6:
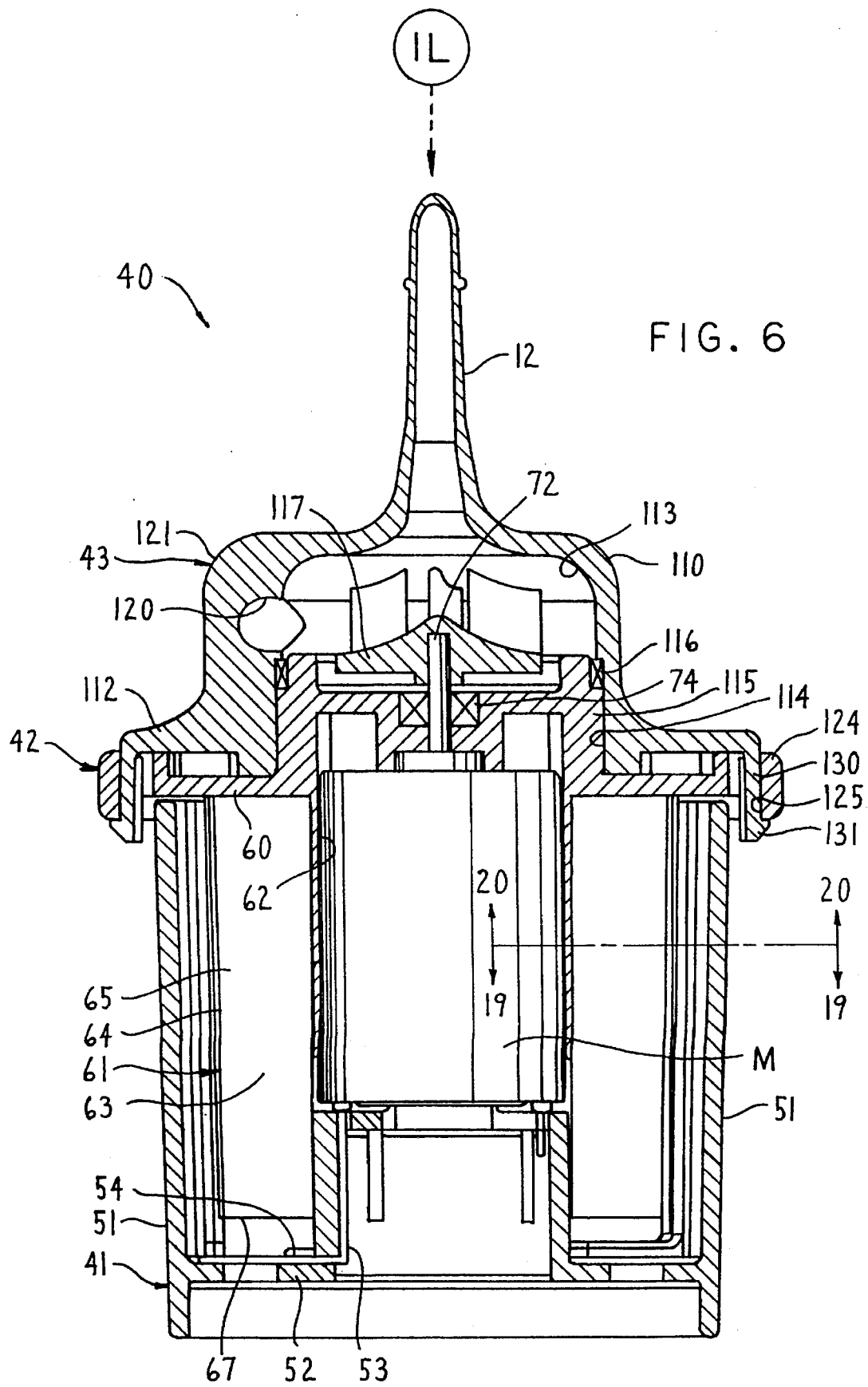
FIG. 6 is a central cross-sectional view similar to FIG. 5 but with the diametral cutting plane rotated to cut through a diametrically opposed pair of depending cover tabs, as generally indicated by the line 6—6 in FIG. 2.

The cover 43 (FIGS. 2–6 and 23–26) includes a downwardly opening dome 110, a radially outward extending bottom flange 112 and the inlet connector 12. The inlet connector 12 takes the form of a hollow spigot upstanding from the top of the dome 110 and, as seen in FIG. 6, provides an irrigation liquid inlet conduit down through the top of the dome 110 and into a pump chamber 113 occupying the upper part of the dome 110. A recess 114 (FIG. 5) is stepped radially outward slightly from the pump chamber 113 and extends downward therefrom through the bottom of the cover 43. The central portion of the deck 60 (FIGS. 2 and 6) protrudes upward to form a relatively large diameter, generally cylindrical plug 115 which is received snugly upward into the downwardly opening recess 114 of the dome 110. A resilient, annular seal 116 (FIG. 6) is trapped vertically between axially opposed steps adjacent the top of the recess 114 and plug 115 to seal the bottom of the pump chamber 113. A preferably conventional centrifugal pump rotor 117 (FIGS. 5 and 6) is fixed coaxially atop the motor shaft 72 in the pump chamber 113. The motor shaft 72 and pump rotor 117 are preferably coaxial with the liquid inlet 12. An outlet passage 120 extends tangentially from the pump chamber 113 within a tangential extension 121 (FIG. 2) of the dome 110 and has an enlarged diameter outlet recess 122 adapted to fixedly sealingly receive therein the end of the irrigation liquid tube 23 as seen for example in FIG. 2, to pump irrigation liquid into the tube 23.

Figure 1:
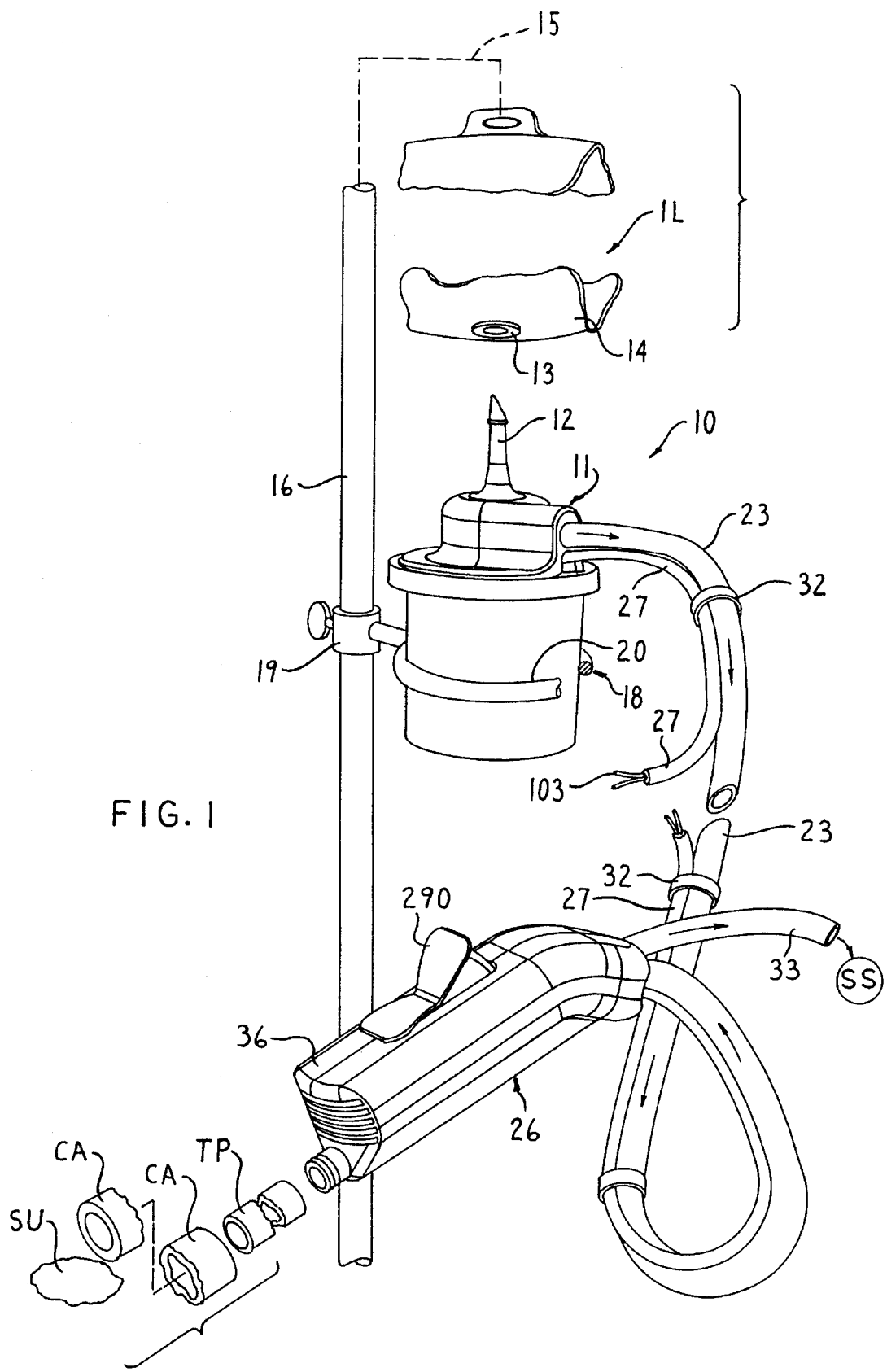
FIG. 1 is a fragmentary, partially broken, somewhat schematic view of a system embodying the invention.

Immediately beneath the outlet recess 122 in the tangential dome extension 121 is a downwardly and radially outwardly opening groove 123 which is blind at its radially inner end. With the cover fixed in its proper location atop the locator 42, the blind groove 123 opens downward into the upper cable port 101 in the deck 60 of the locator 42, to route the cable 27 (FIG. 5) upward and radially outward and away from the pressure liquid unit 11 and along the path of the irrigation liquid tube 23, as generally indicated in FIG. 1.

The cup 41 and locator 42 and cover 43 are fixed together, preferably by snap fit connections, as follows. The deck 60 (FIG. 4) has an upwardly and downwardly thickened rim 124. Radially inboard from the rim 124, the deck 60 is axially punctured by circumferentially extending, circumferentially spaced slots 125 and 126. The slots 125 alternate circumferentially with the slots 126

Circumferentially spaced, generally L-profile tabs 130 each depend slightly bendably from the perimeter edge of the cover 43 and insert downward into a respective slot 125 in the deck 60. Each tab 130 has a radially outward extending lip 131 (FIGS. 4 and 6) which snaps radially outward under the deck rim 124 to hold the cover 43 fixed downward firmly against the deck 60 of the locator 42.

Figure 4:
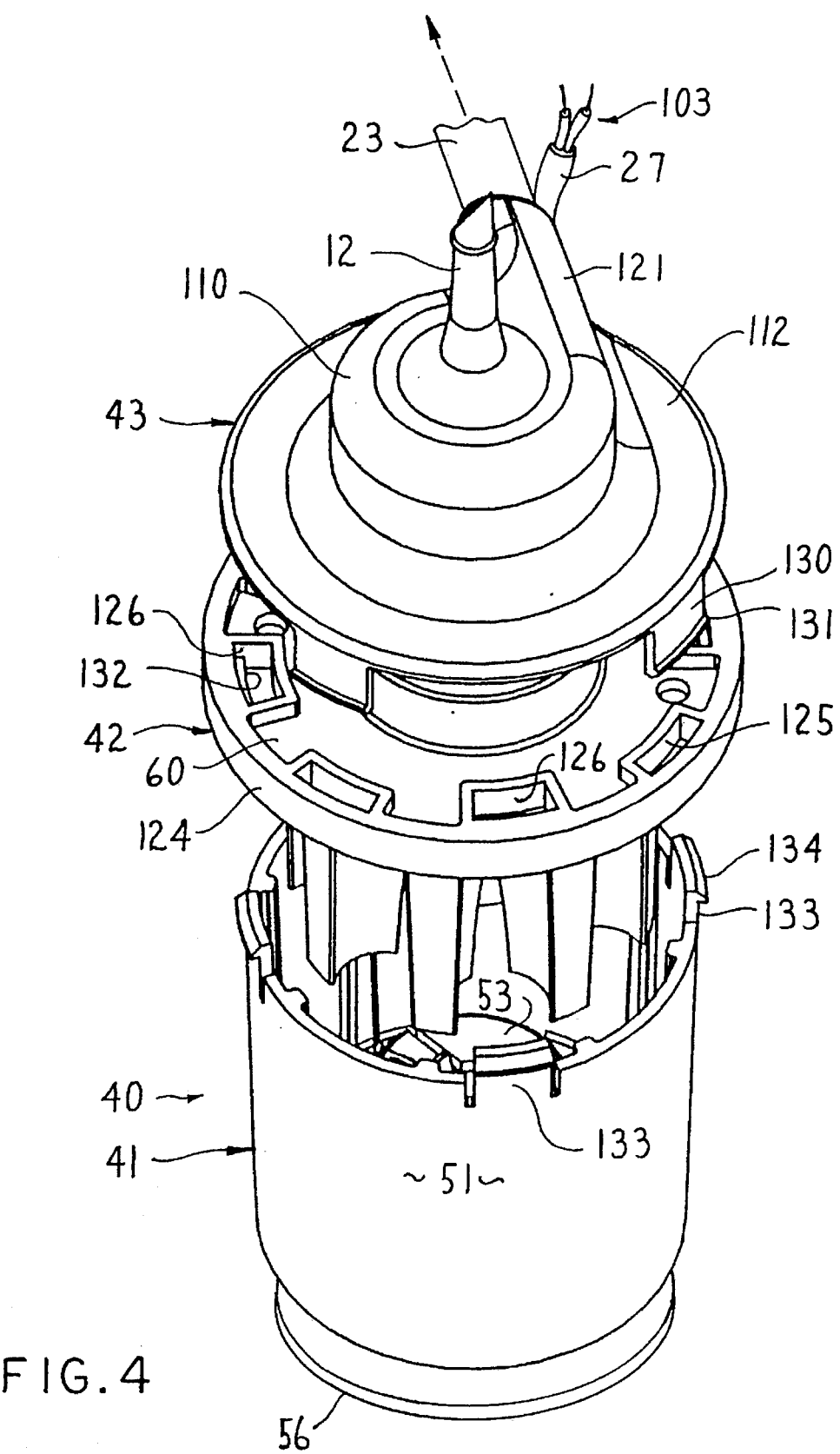

The slots 126 each have a circumferentially extending step 132 upset radially inward from the rim 124 near the bottom of such slot 126, as indicated for example in FIGS. 4 and 13. Circumferentially spaced tabs 133 extend up from the sidewall 51 of the cup 41 and are generally L-shaped, each having a shallow radially outward extending lip 134. The tabs 133 are circumferentially in register with the remaining slots 126 in the locator deck 60. Upon bringing the cup 41 upward coaxially toward the deck 60, the tops of the tabs 133 enter the slots 126. As the top of the cup 51 moves into contact with the underside of the deck 60, the tab lips 134 each advance upward past, and are deflected resiliently radially inward by, the corresponding step 132 to snap over such step 132.

In this way, the tabs 130 and 133, properly lodged in their slots 125 and 126 maintain the cup 41, locator 42 and cover 43 rigidly fixed in assembled relation, as seen in FIG. 1, together.

While the cup 51, locator 42 and cover 43 may be of any desired rigid material and manufactured in any desired way it is convenient to mold same each in one piece, of a conventional plastics material.

A circular, disk-like label of generally rigid material, such as cardboard, styrofoam, or the like, fits snugly up into the downward opening recess 55 (FIG. 3) defined by downward extension of the sidewall 51 a short distance below the bottom wall 52. Such label may be fixed in place as a last step in the assembly operation, by adhesive bonding or by press fit upward into the recess 55 due to the slight downward taper of the cup side wall 51. A suitable disk is indicated at 56 in FIGS. 4 and 5. The disk 56 can be used to cover holes in the bottom wall 52 and wiring between the cable 27 and motor contacts MC and battery lower contacts 93. Such disk 56 could also be used as a label for describing the product, usage and warnings regarding misuse.

Figure 16:
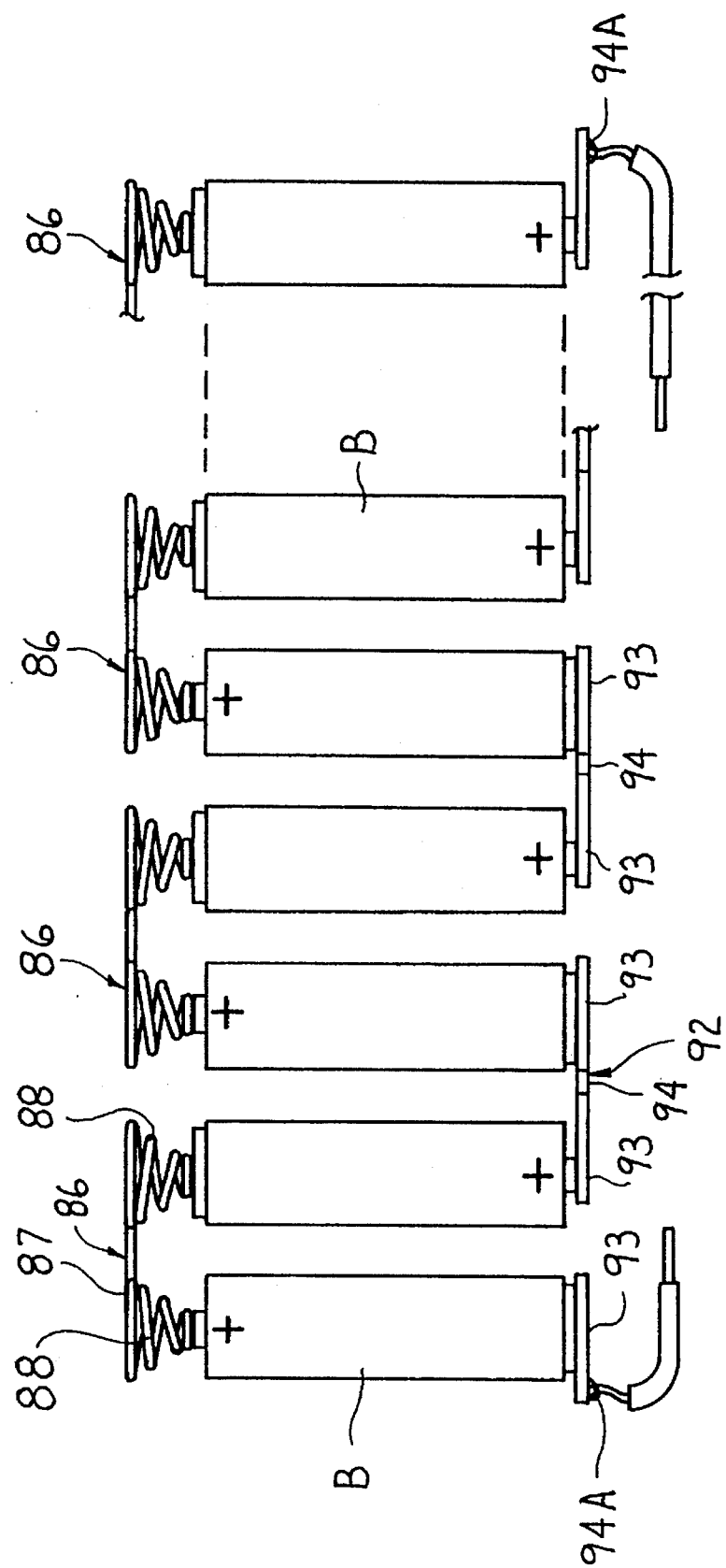
FIG. 16 is a schematic elevational view of the electrical connections for batteries to be carried by the FIG. 13 locator.
Figure 22:
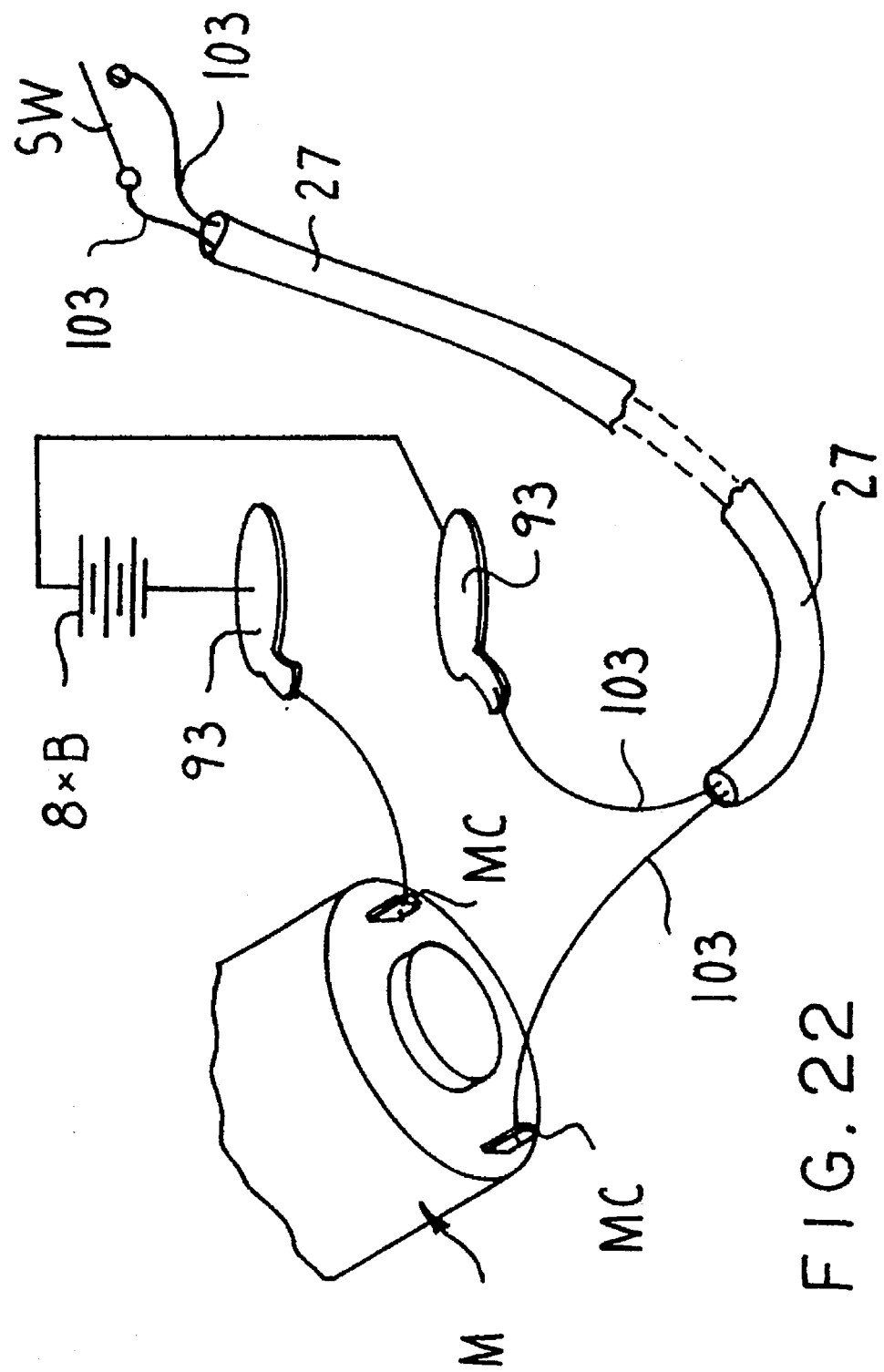
FIG. 22 is a schematic representation of the electrical circuit of the FIG. 1 system.
Figure 23:
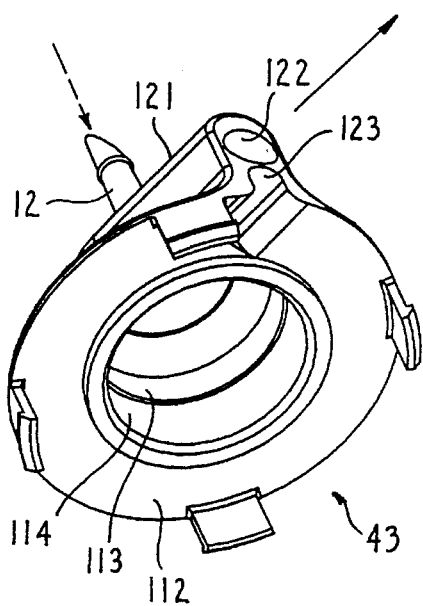
FIGS. 23–25 are pictorial views of the pumping chamber cover of the FIGS. 2–4 apparatus, taken from the underside in FIGS. 23 and 24 and from the top in FIG. 25.
Figure 24:
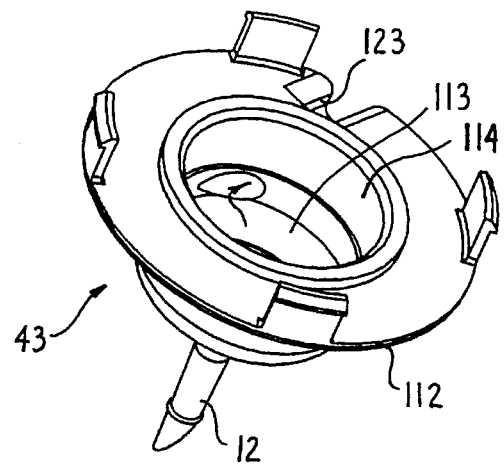
Figure 25:
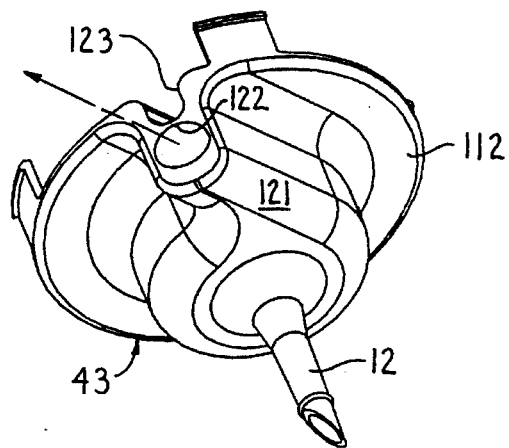
Figure 26:
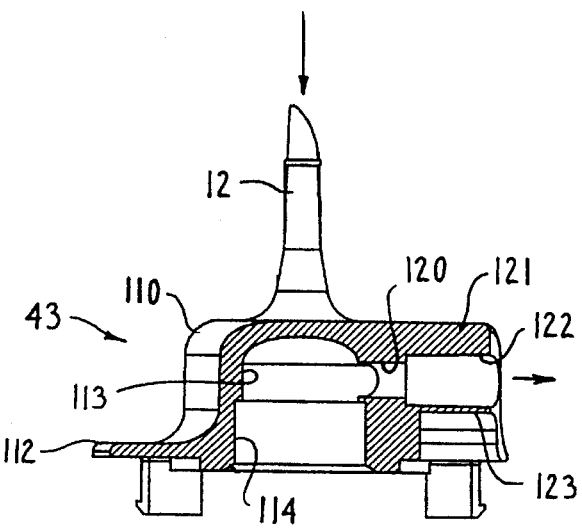
FIG. 26 is a side elevational view of the FIG. 23 cover partially broken on a cutting plane including the central axis of the liquid outlet and cable groove.

The spring wire upper contacts 86 and lower contact disks 93 are located to connect the eight batteries B in series, as seen in FIG. 16 and as schematically indicated at 8 X B in the FIG. 22 circuit diagram. The series battery connection 8 X B is in turn connected in series loop (through the endmost disks 93) with the motor M (through its contacts MC) and (through the conductors 103 of the cable 27) with the manually actuable switch SW (hereafter described, in the handpiece 26) as shown in FIG. 22.

Handpiece 26

Figure 27:
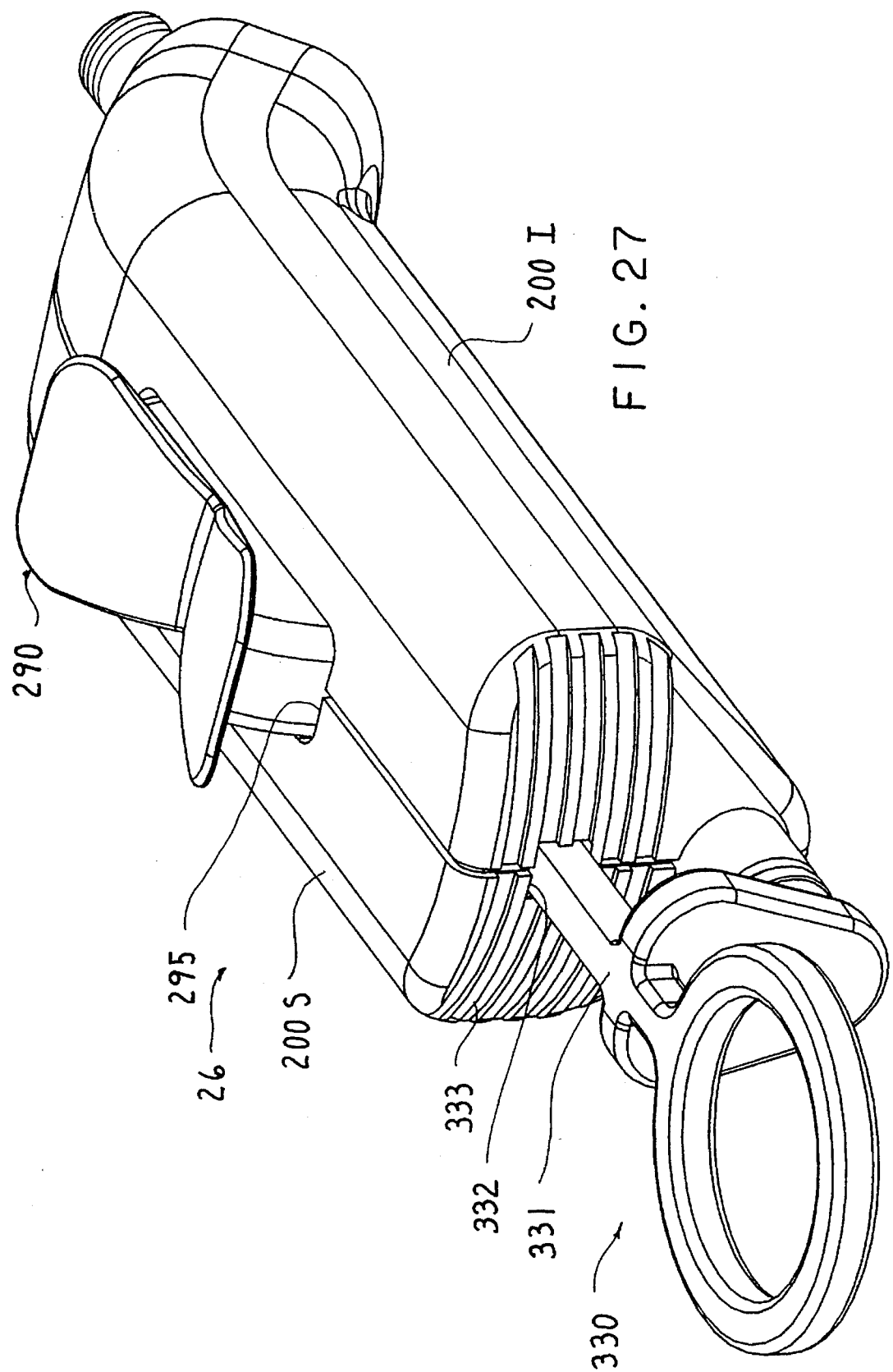
FIG. 27 is a pictorial view of the handpiece of FIG. 1 with the user actuated rocker in neutral (rest) position and the guard pin inserted for packing or shipping.
Figure 28:
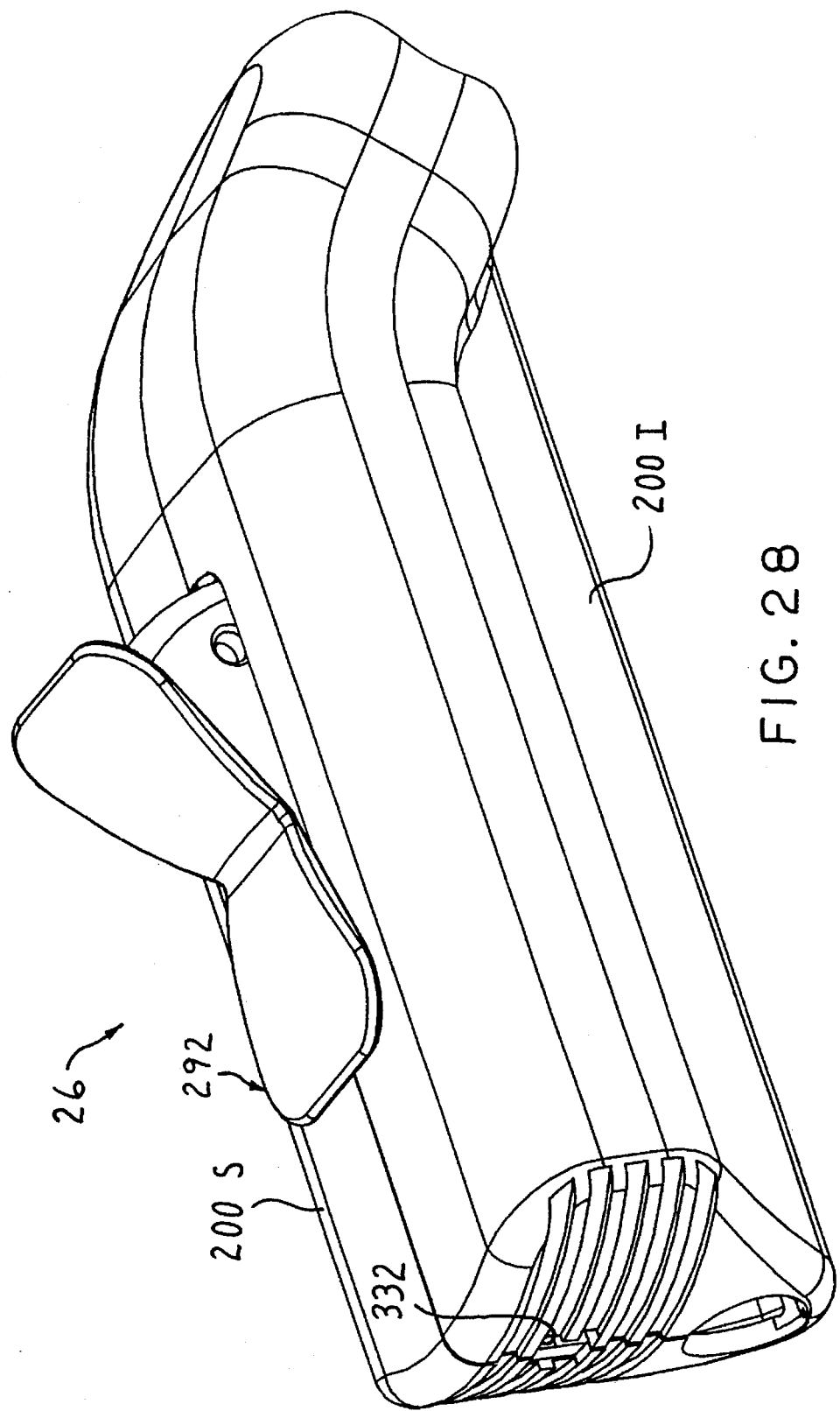
FIG. 28 is a pictorial view generally similar to FIG. 27 but taken at a different angle and omitting the guard pin and the conduit and with the rocker tilted forward.
Figure 29:
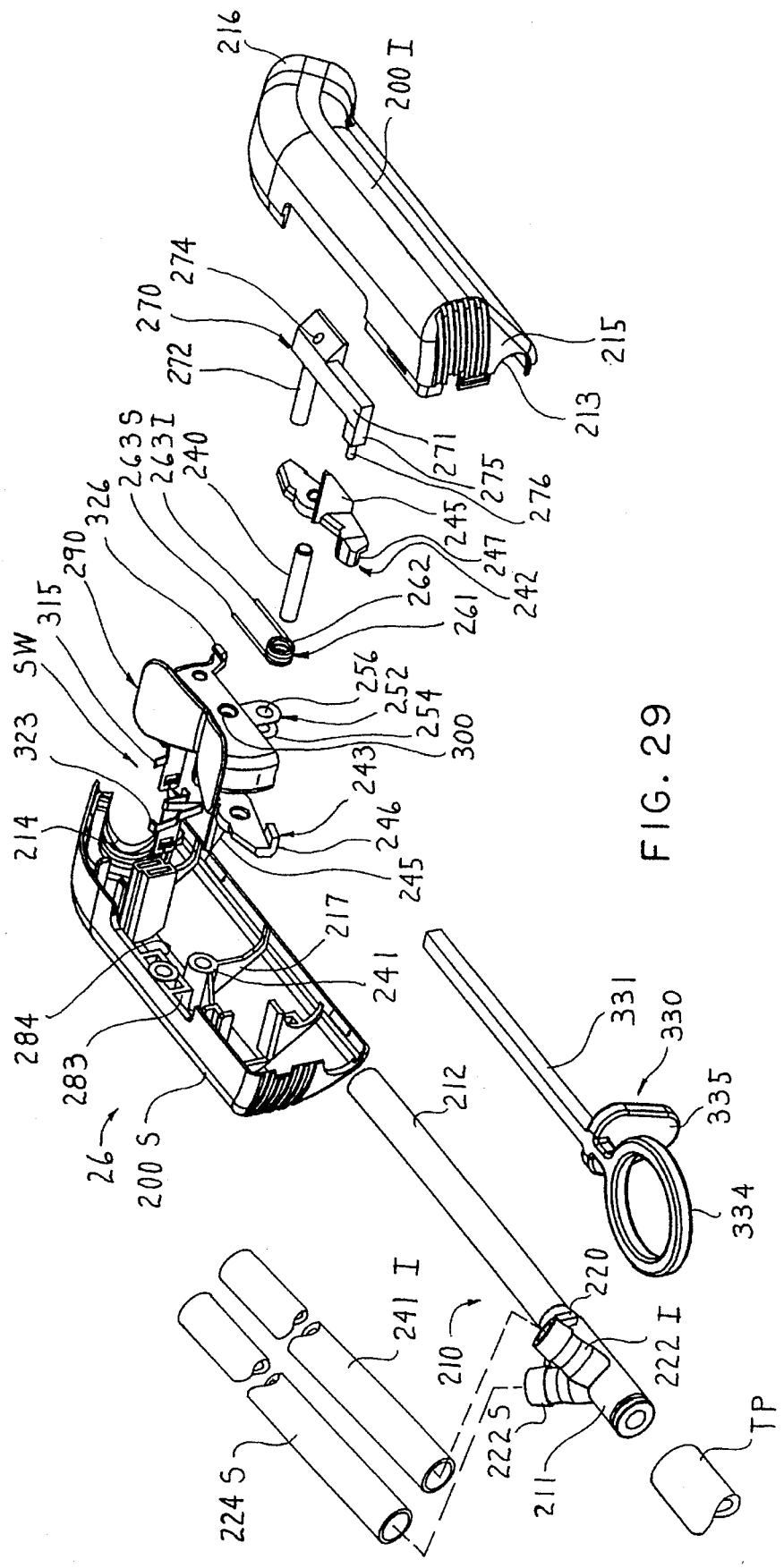
FIG. 29 is an exploded view of the FIG. 21 handpiece drawn in reduced scale and omitting the adapter block at the rear thereof.
Figure 30:
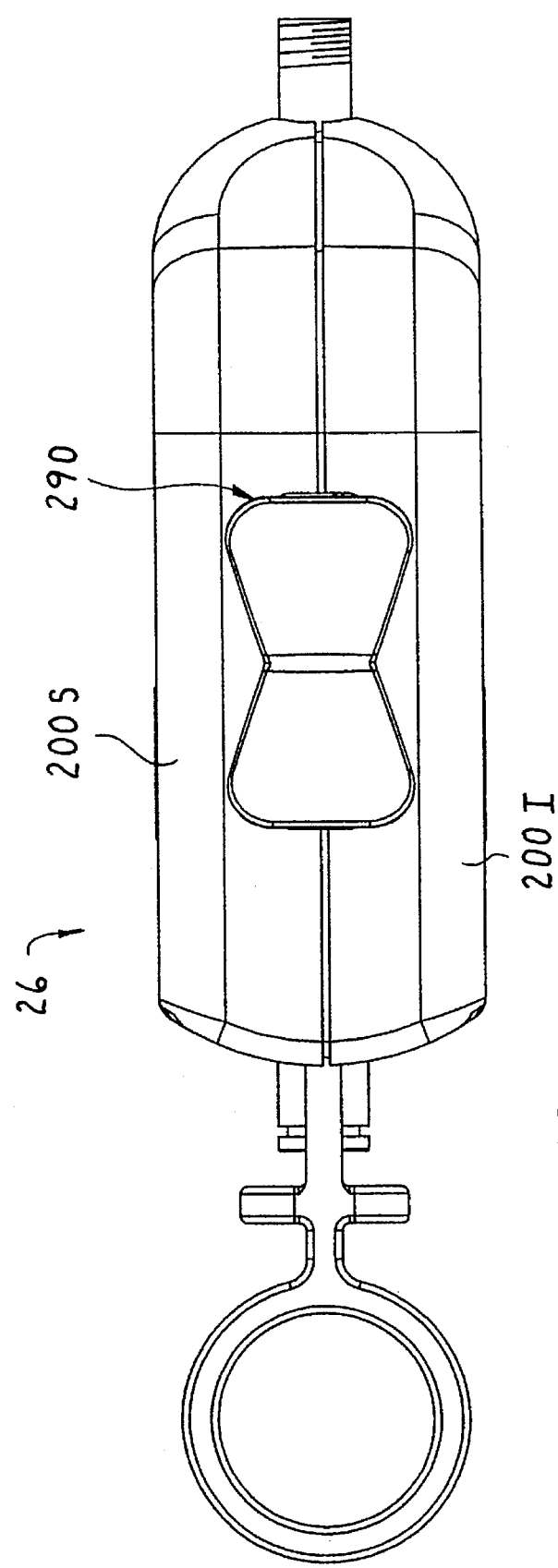
FIGS. 30 and 31 are respective top and bottom views of the FIG. 27 handpiece.
Figure 31:
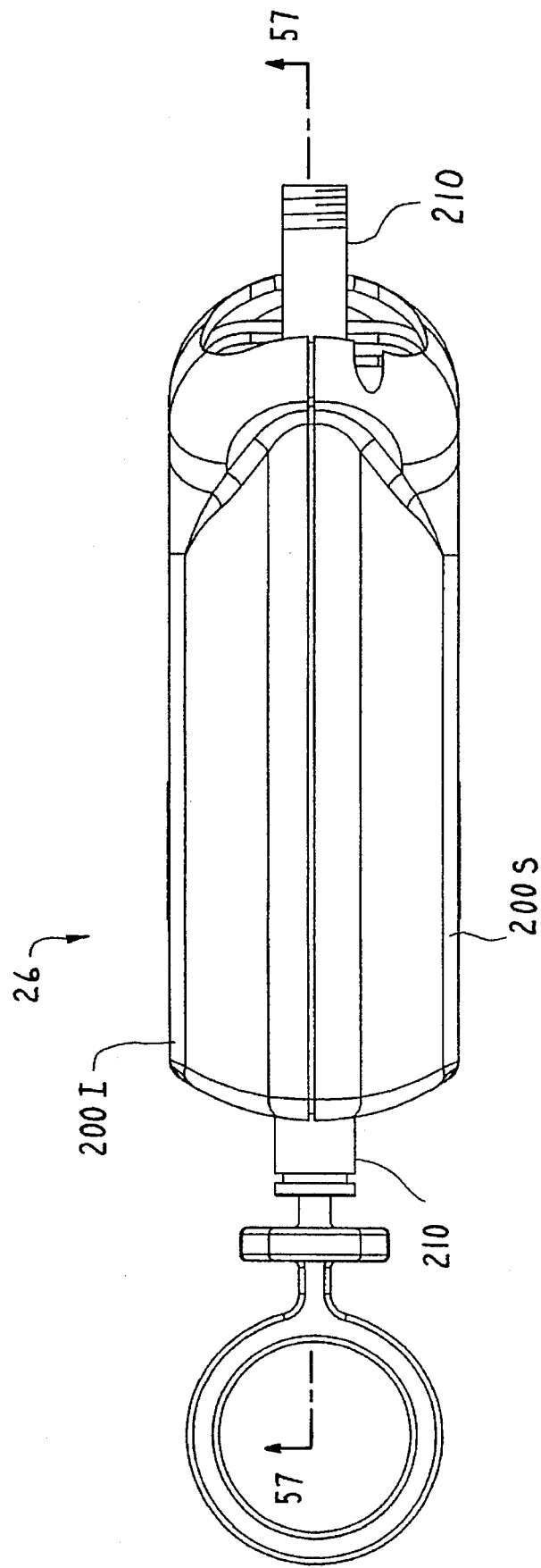

The handpiece 26 comprises an outer shell conveniently defined by opposed concave half shells 200S and 200I located respectively on the suction and irrigation sides of the handpiece, as generally indicated in FIGS. 27–29. In the finished handpiece, the edges 201 of the half shell 200S overlap edges 202 of the half shell 200I (FIGS. 33–38) and are fixed thereto by any convenient means such as conventional snapfit connections 203 and 204 respectively, or by adhesive bonding, or the like.

Figure 57:
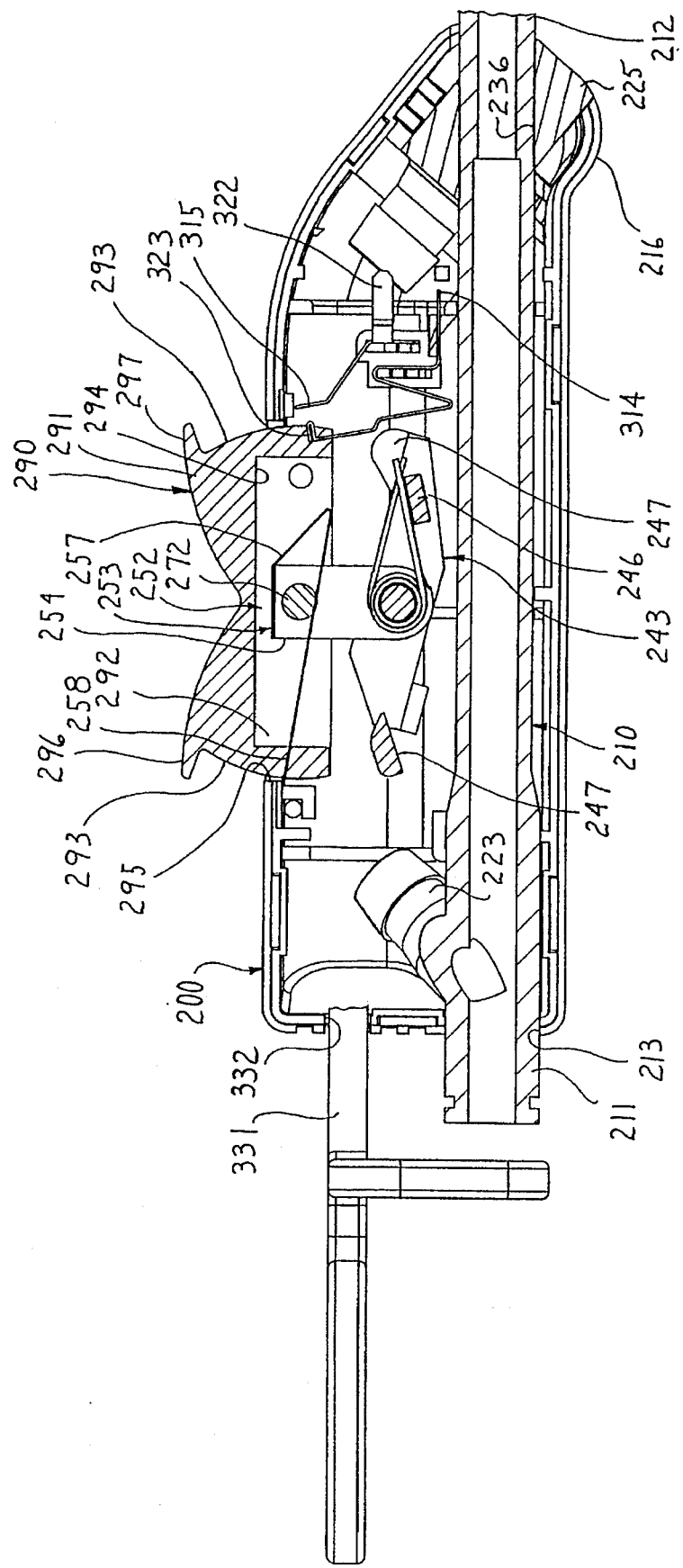
FIG. 57 is a central cross-sectional view substantially as taken on the line 57—57 of FIG. 31 with the rear portion of the guard pin broken away.
Figure 58:
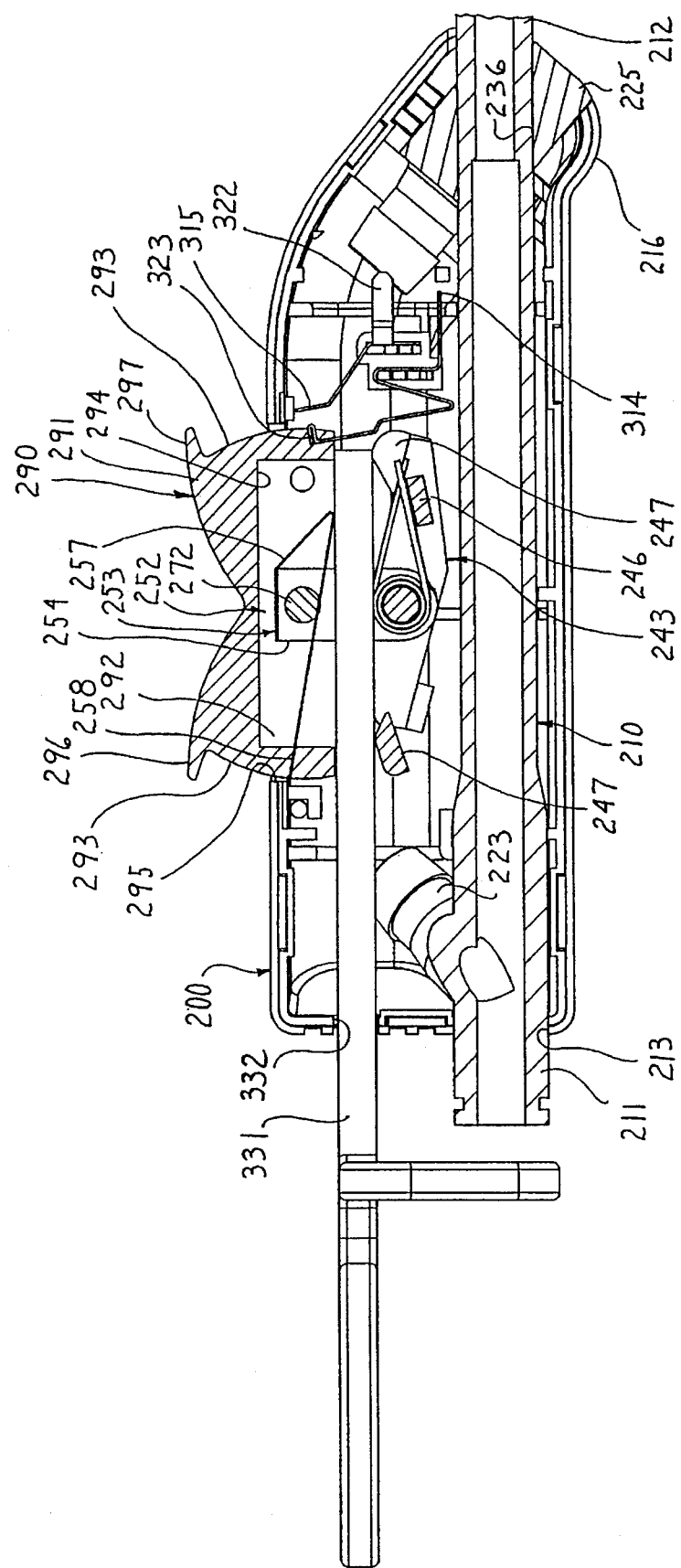
FIG. 58 is a view similar to FIG. 57 but showing the entire guard pin in place.

An elongate rigid conduit 210 extends longitudinally through the lower portion of the shell 200 and has front and rear end portions 211 and 212 which respectively protrude forwardly and rearwardly through front and rear openings 213 and 214 respectively in the substantially radial front wall and in the somewhat downward angled rear end portion 268 of the shell 200 (FIGS. 29 and 57). Longitudinally spaced ribs 217 in the half shells 200S and 200I radially fix conduit 210 therein. Transversely extending tabs 20 (FIGS. 44 and 45) fixed on the conduit 210 are received in ports 221 (FIGS. 35 and 38) opening toward each other in the half shells 200S and 200I to locate the conduit longitudinally fixedly in the shell 200, as seen for example in FIG. 29.

Conventionally annularly ribbed, hollow, tubular suction and irrigation fittings 222I and 222S (FIG. 29) rigidly connect to the front portion 211 of the rigid conduit 210 inside the shell 200, adjacent the front wall 215 thereof as seen in FIG. 53. The fittings 222S and 222I diverge upwardly and angle rearwardly for fixed securement thereon of respective resiliently pressurably closeable, normally open hoses 224S and 224I (FIG. 29).

The downward and rearward angled rear opening 214 of the shell 200 is normally occupied by an adapter block 225 (FIGS. 42, 43, 53 and 57) fixed into the rear opening 214 (FIG. 53) of the shell 210 during assembly of the two half shells 200S and 200I. More particularly, the adapter block 225 (FIGS. 42 and 43) has laterally protruding, partially circumferentially extending, locator ribs 226 fixed thereon. Reception, during assembly of the half shells together, of the ribs 226 snugly between a forward/rearward spaced pair of further ribs 227 (FIGS. 35 and 38) circumferentially extending in the rear end portion 212 of the half shells 200S and 200I, fixes the adapter block 225 within the shell 200. The adapter block further comprises a laterally spaced pair of generally upwardly and forwardly aimed, externally ribbed fittings 230S and 230I (FIGS. 42 and 43) for receiving thereon, in fixed liquid tight coupled relation, the rear ends of the pinchable hoses 224S and 224I respectively. The fittings 230S and 230I are similar in form to the fittings 222S and 222I above discussed. Passages indicated in broken lines at 231 extend from the open front of the fittings 230S and 230I rearward through the adapter block and open through the rear end face 232 thereof and are adapted to fixedly and nonleakingly receive, in any conventional manner not shown, the front ends of the suction tube 33 and irrigation liquid tube 23, as indicated in FIGS. 42 and 43.

Figure 32:
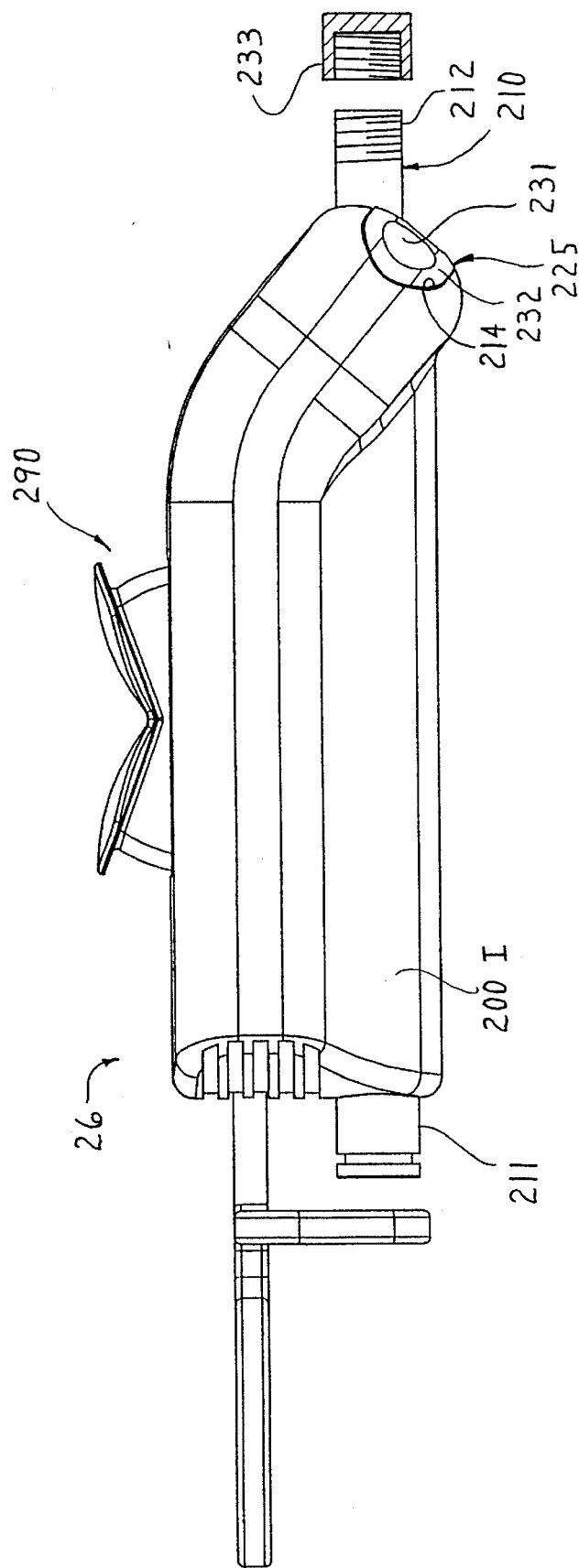
FIG. 32 is a side elevational view of the FIG. 27 handpiece.
Figure 33:
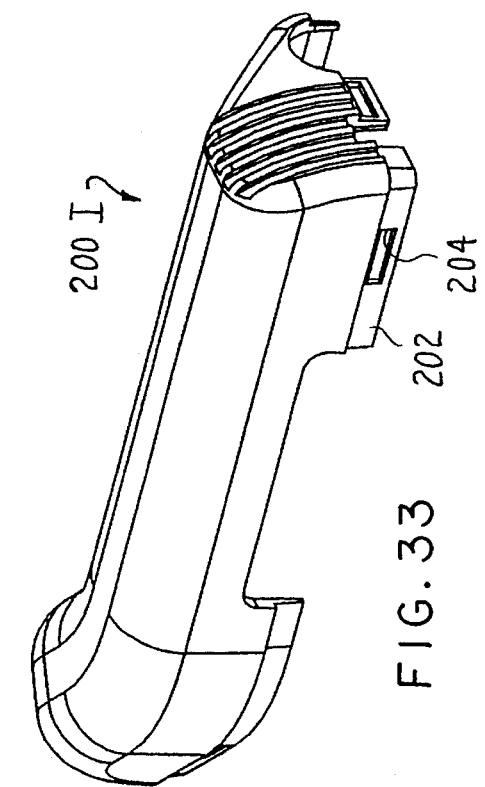
FIGS. 33 and 34 are pictorial views of the irrigation side half shell of the FIG. 27 handpiece.
Figure 34:
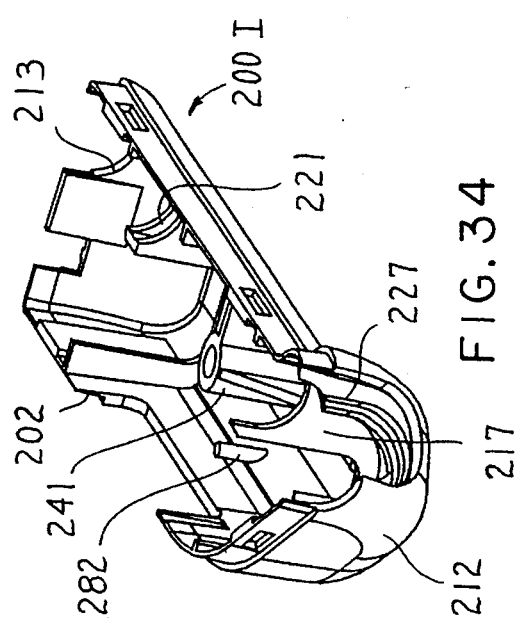

The rear end portion 212 of the rigid conduit 210 may be closed by a cap 233 (FIG. 32) releasably secured thereon, by any convenient means such as threads. Alternatively, the cap 233 may be removed to enable insertion forwardly through the conduit 210 of an elongate instrument, or other aid to surgery, whose front end is to be positioned adjacent the surgical site.

The hollow cylindrical tip TP (FIG. 53) is mountable removably on the front end portion 211 of the rigid conduit 210. An O-ring 234 or the like in an annular groove 235 in the conduit sealingly engages the hollow tip TP fixedly to the front end of the conduit 210.

The rear end portion 212 of the rigid conduit 210 passes snugly, but slidably, rearward through a central hole 236 in the adapter block 225 (see FIGS. 42, 43 and 57).

Figure 35:
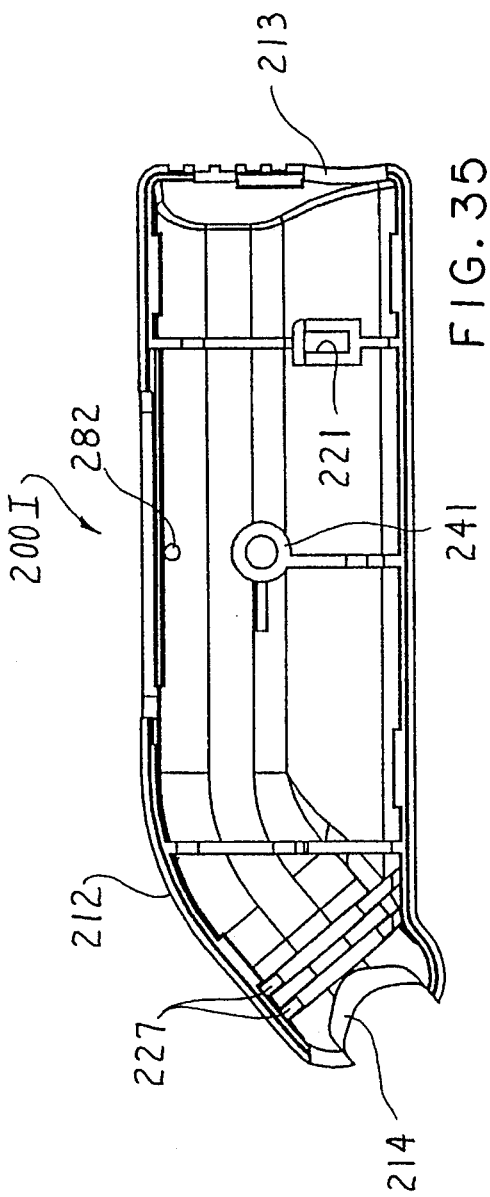
FIG. 35 is a side elevational view, taken from the inside, of the FIG. 33 half shell.
Figure 38:
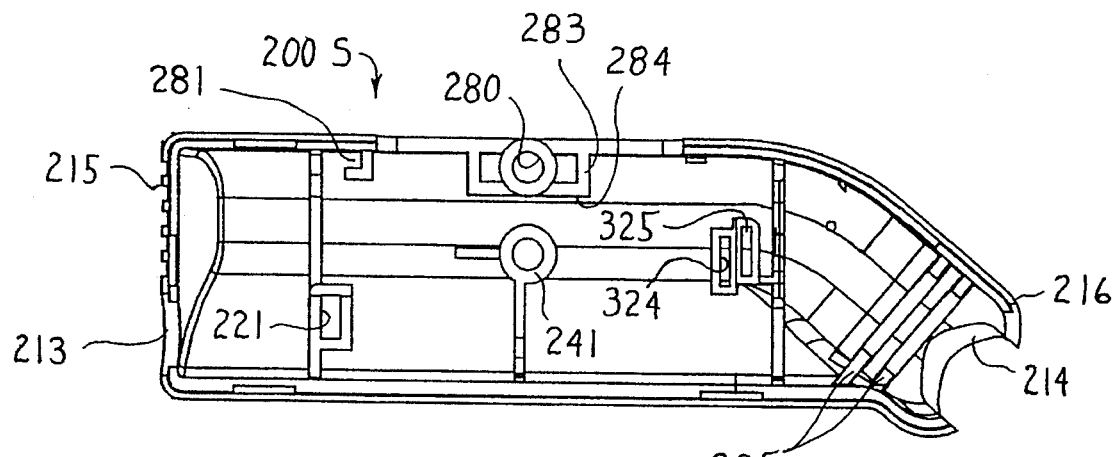
FIG. 38 is an elevational view of the FIG. 37 half shell.
Figure 37:
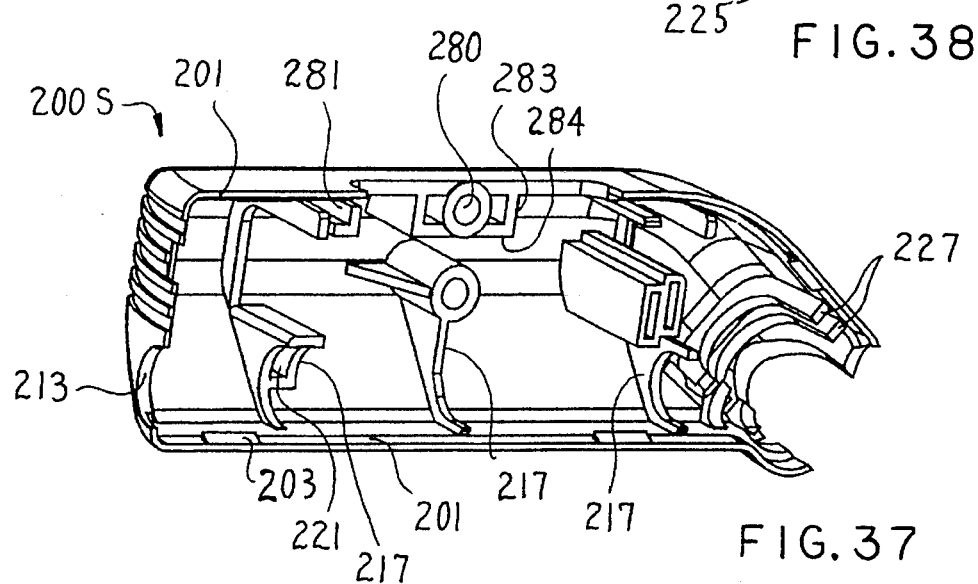
FIGS. 36 and 37 are pictorial views of the other half shell of the FIG. 27 handpiece.
Figure 36:
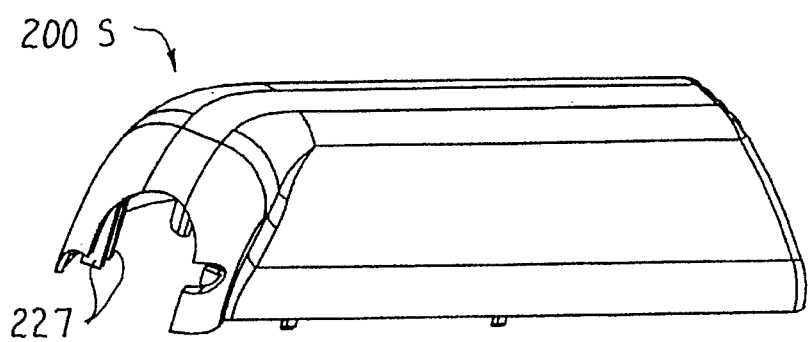

A transverse shaft 240 (FIG. 29) extends across the interior of the shell 200 and has its ends fixed in transversely opposed, tubular bosses 241 (FIGS. 29, 35 and 38). The shaft 240 is located about mid-height in the shell 200.

An irrigation pinch lever 242 and a suction pinch lever 243 (FIG. 29) are located on the shaft 240, adjacent the irrigation half shell 200I and suction half shell 200S respectively. The pinch levers each have mid portions pivoted on the shaft 240 and each extends forward and rearward from the shaft. As seen in FIGS. 40 and 41 the levers 242 and 243 each have a through bore 244 for pivoting on the shaft 240 a round edged pinch blade 245 extending from one side thereof adjacent the bore 244, and a pair of tabs 246 and 247 extending from the other side thereof at respective opposite ends thereof. In the embodiment shown, the tabs 246 are flat and the tabs 247 are domed. In the preferred embodiment shown, the pinch levers 242 and 243 differ only in that the domed tab 247 of the irrigation pinch lever 242 is somewhat flattened, as seen at 248 (FIG. 41). As seen in FIG. 29, the pinch levers 242 and 243 are each assembled on the shaft 240 so that the elongate pinch edge 249 of the blade 245 faces upward but wherein the two pinch blades 245 extend laterally away from each other and toward their respective half shells 200S and 200I. Thus, the pinch levers 242 and 243 are oriented on the shaft 240 such that their respective tabs 247 and 246 are forwardmost (leftwardmost in FIG. 29).

Figure 47:
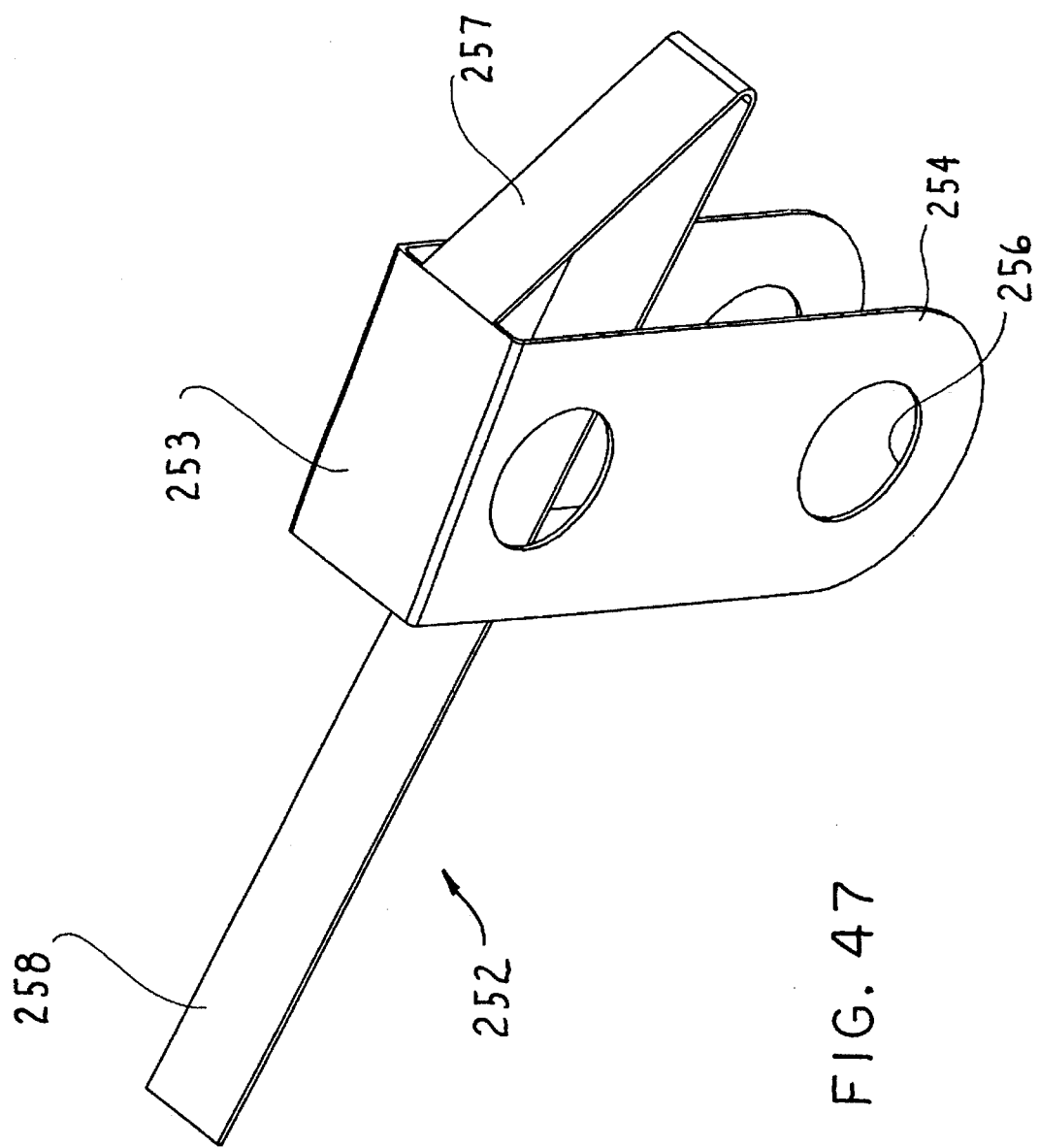
FIGS. 47, 48 and 49 are substantially enlarged pictorial views of the U-spring, switch spring and Z-spring, respectively, of FIG. 29.

A resilient metal U-spring 252 (FIGS. 29 and 47) of springy sheet metal comprises a U-shaped portion 253 comprising a pair of legs 254 depending from a bight 255. Holes 256 through the lower portion of the legs 254 receive the shaft 240 to pivotly locate the U-spring 252 on the shaft 240 snugly between the pinch levers 242 and 243 and with the bight 255 spaced up above the shaft 240. A leaf spring-like arm 257 extends rearward and downward from the bight 255. The free end portion 258 of the arm 257 is bent sharply to extend forward and somewhat upward between the legs 254 in spaced relation between the bight 255 and holes 256.

Figure 52:
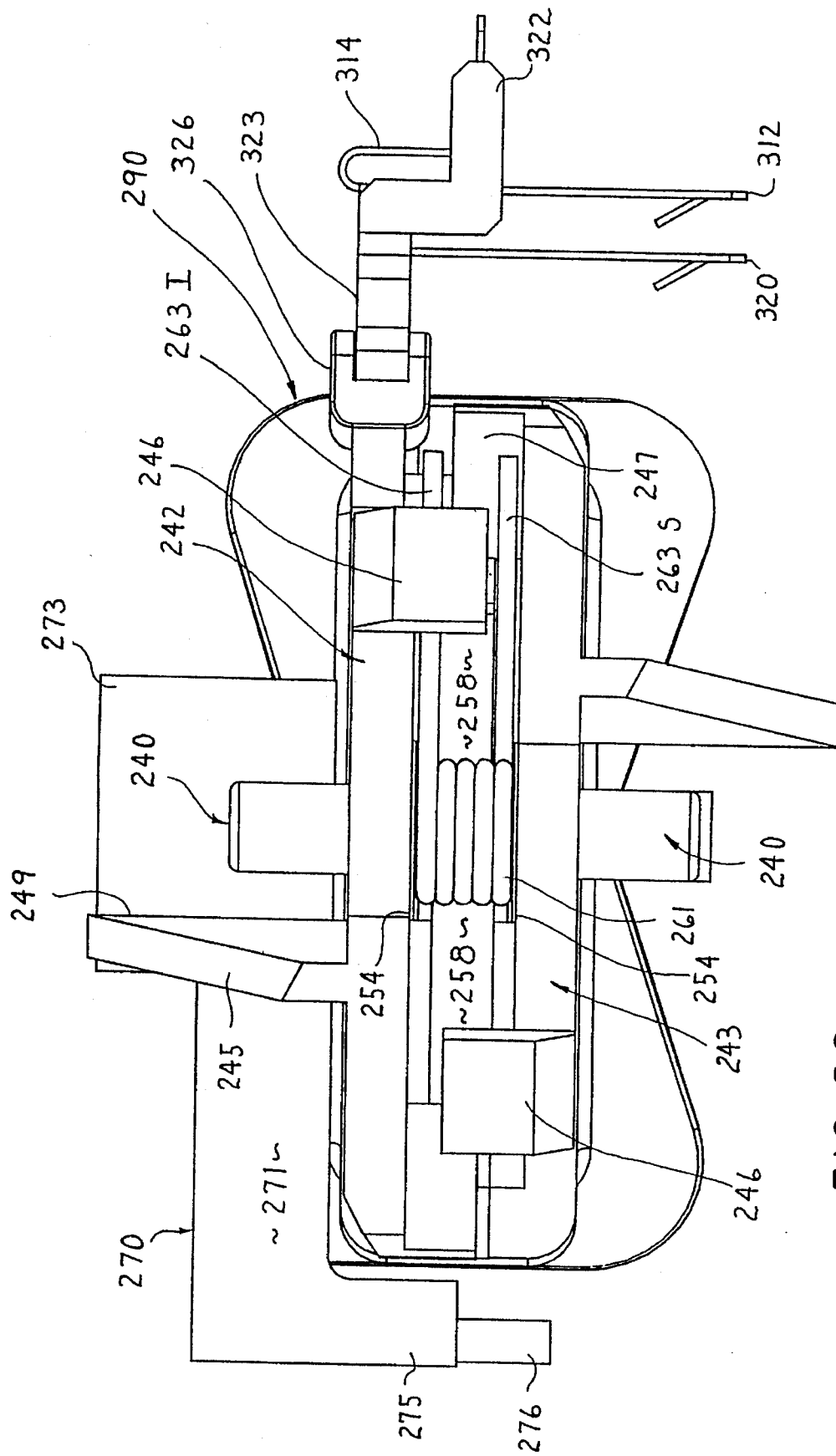
FIG. 52 is an enlarged bottom view of the FIG. 50 subassembly.
Figure 54:
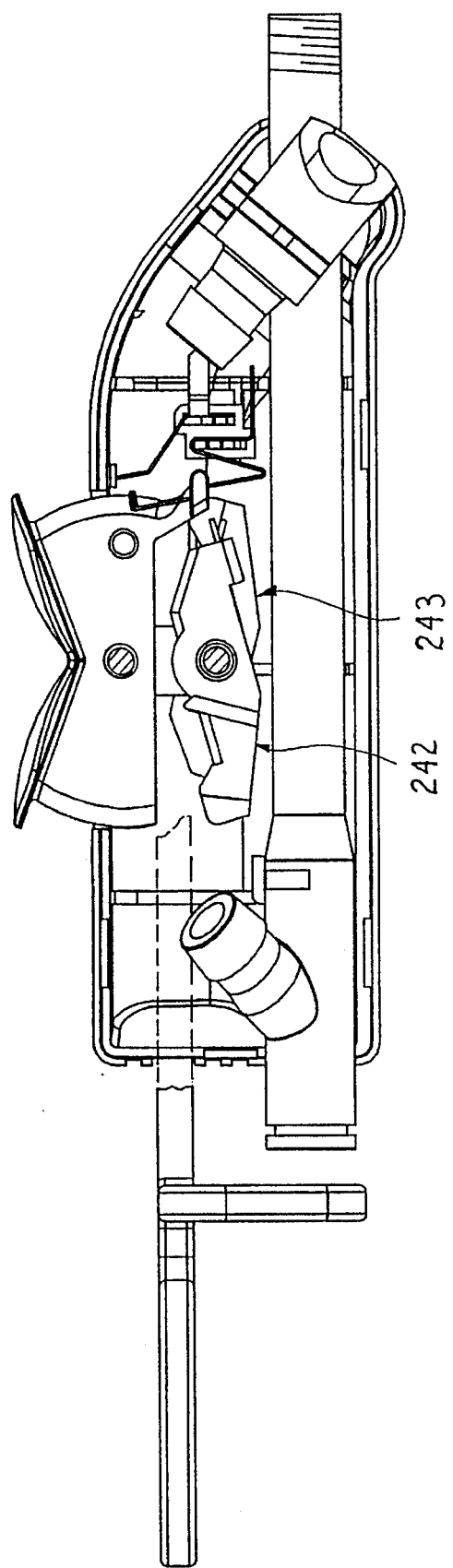
FIG. 54 is a view similar to FIG. 53 but with the irrigation anvil removed.
Figure 55:
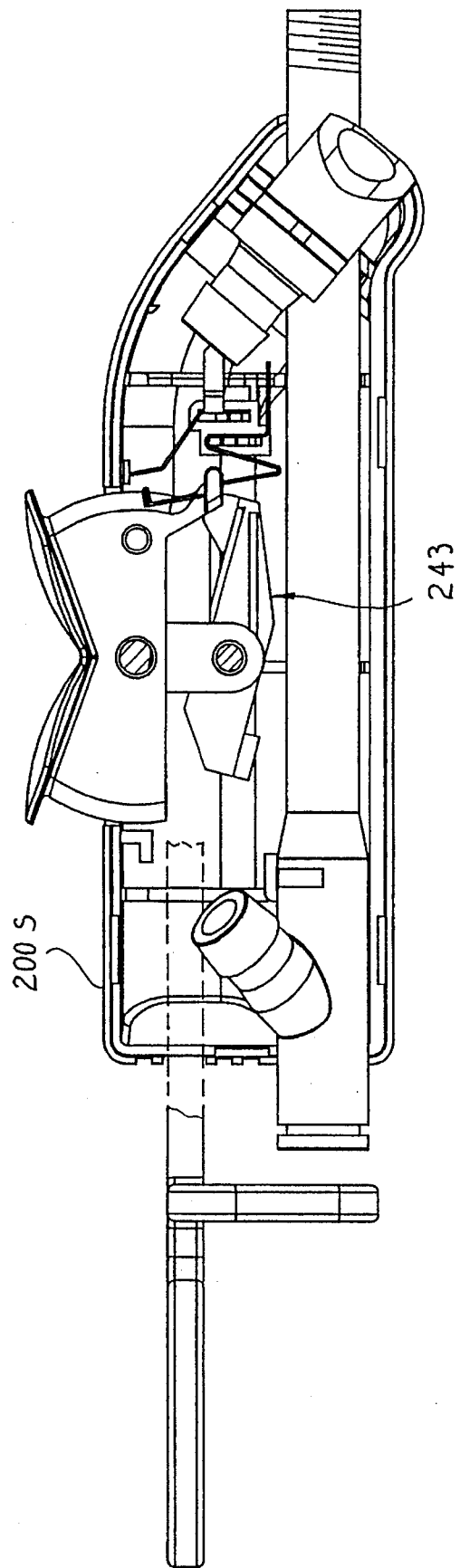
FIG. 55 is a view similar to FIG. 54 but with the irrigation pinch lever removed to show parts behind it.

A coil torsion spring 261 (FIG. 29) comprises a central portion 262 wrapped around the shaft 240 between the U-spring legs 254 and from which central portion extends a pair of generally rearwardly extending elongate legs 263I and 263S which are vertically trapped between and resiliently urge vertically apart the rear tabs 246 and 247 of the pinch levers 242 and 243 (FIGS. 52 and 53).

A rigid, preferably unitary, anvil 270 (FIGS. 29 and 39) comprises a fore/aft extending bar 271 locatable between the half shells 200S and 200I (FIG. 29) and spaced above the shaft 240. At the rear end portion of the bar 271, a horizontal shaft 272 (FIG. 39) extends toward the half shell 200S. The bar is widened toward the half shell 200I to form a downwardly stepped, downwardly facing anvil surface 273. A hole 274 in the rear end portion of the bar 271 is coaxial with the shaft 272 and faces in the opposite direction, namely toward the half shell 200I. The bar 271 is generally L-shaped, as seen from above, having a leg 275 aimed toward the half shell 200S and terminating in a pin 276. In the assembled handpiece. 26, the anvil 270 is fixed with respect to half shell 200S by entry of the free end of its shaft 272 and the pin 276 into corresponding holes 280 and 281 in, and adjacent the top of, the half shell 200S (FIGS. 29, 37 and 38) and by entry of a pin 282 (FIGS. 34 and 35), fixed within the opposite half shell 200I just below the top thereof, into the opposed hole 274 in the rear portion of the anvil 270. In this manner, the anvil 270 is firmly fixed within the assembled shell 200. The anvil 270 is spaced above the irrigation pinch lever 242, with its down facing anvil surface 273 directly opposing the upfacing pinch edge 249 of the pinch blade 245 of the irrigation pinch lever 242 (FIGS. 52 and 53) for coaction therewith in pinching and unpinching the irrigation hose 224I which is routed therebetween.

A further anvil, which may termed the suction anvil, 283 (FIGS. 29, 37 and 56) is fixed in and preferably formed integrally with the half shell 200S and has a down facing anvil surface 284 underlying the upper shaft hole 280 and at about the same height as the anvil surface 273 cooperating with the irrigation pinch lever 242 above-described. The down facing anvil surface 284 overlies and cooperates with the upfacing pinch blade edge 249 of the suction pinch lever 243 for pinching and unpinching the suction hose 224S routed therebetween.

Figure 50:
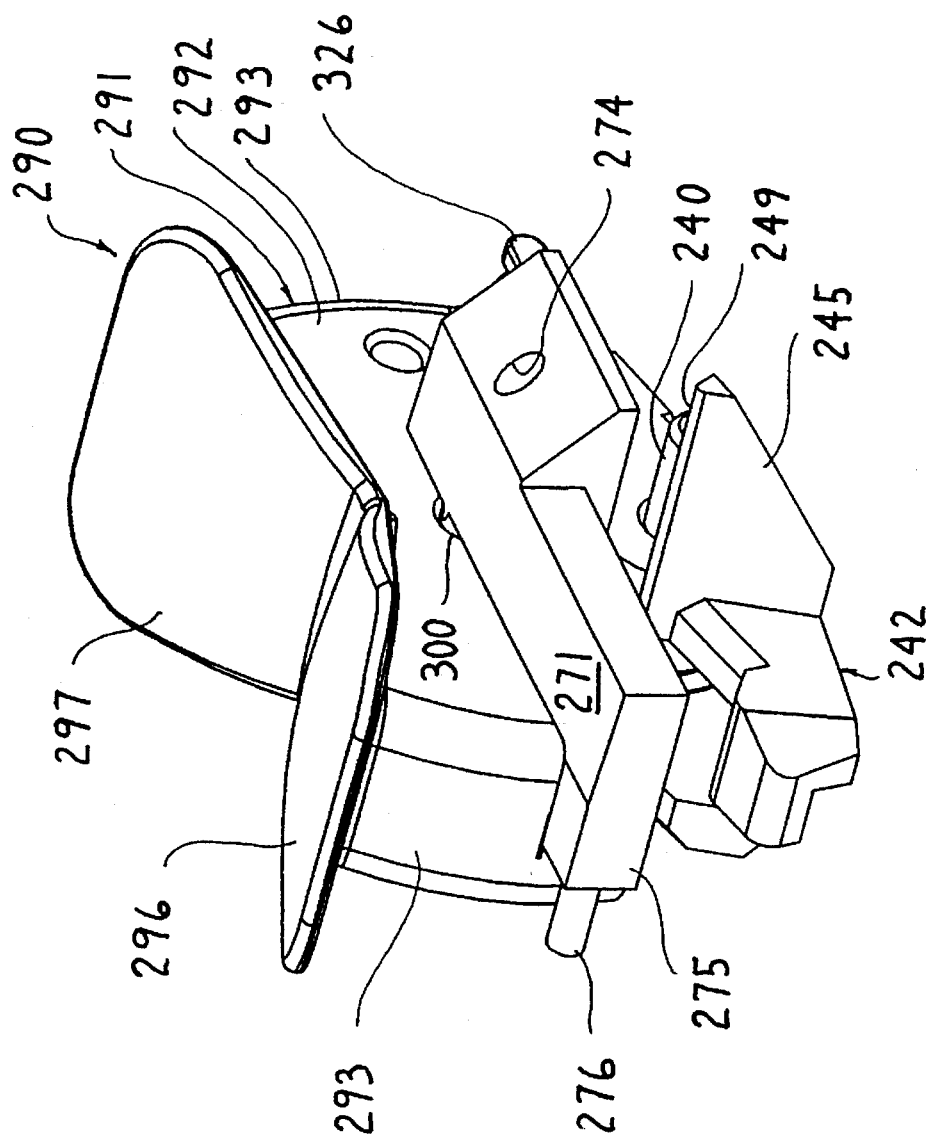
FIG. 50 is an enlarged pictorial view of a subassembly of the FIG. 29 handpiece.

A hand actuable rocker 290 (FIG. 29) comprises a generally box-like body 291 (FIG. 50) having parallel upstanding side walls 292 and convexly rounded, upwardly converging front and rear end walls 293. The body 291 includes a relatively large, generally rectangular, downwardly opening recess 294 (FIG. 57). The body 291 extends down through an opening 295 in the top of the shell 200. The body is topped by fixed, preferably integral, divergently angled, front and rear push pads 296 and 297.

Figure 56:
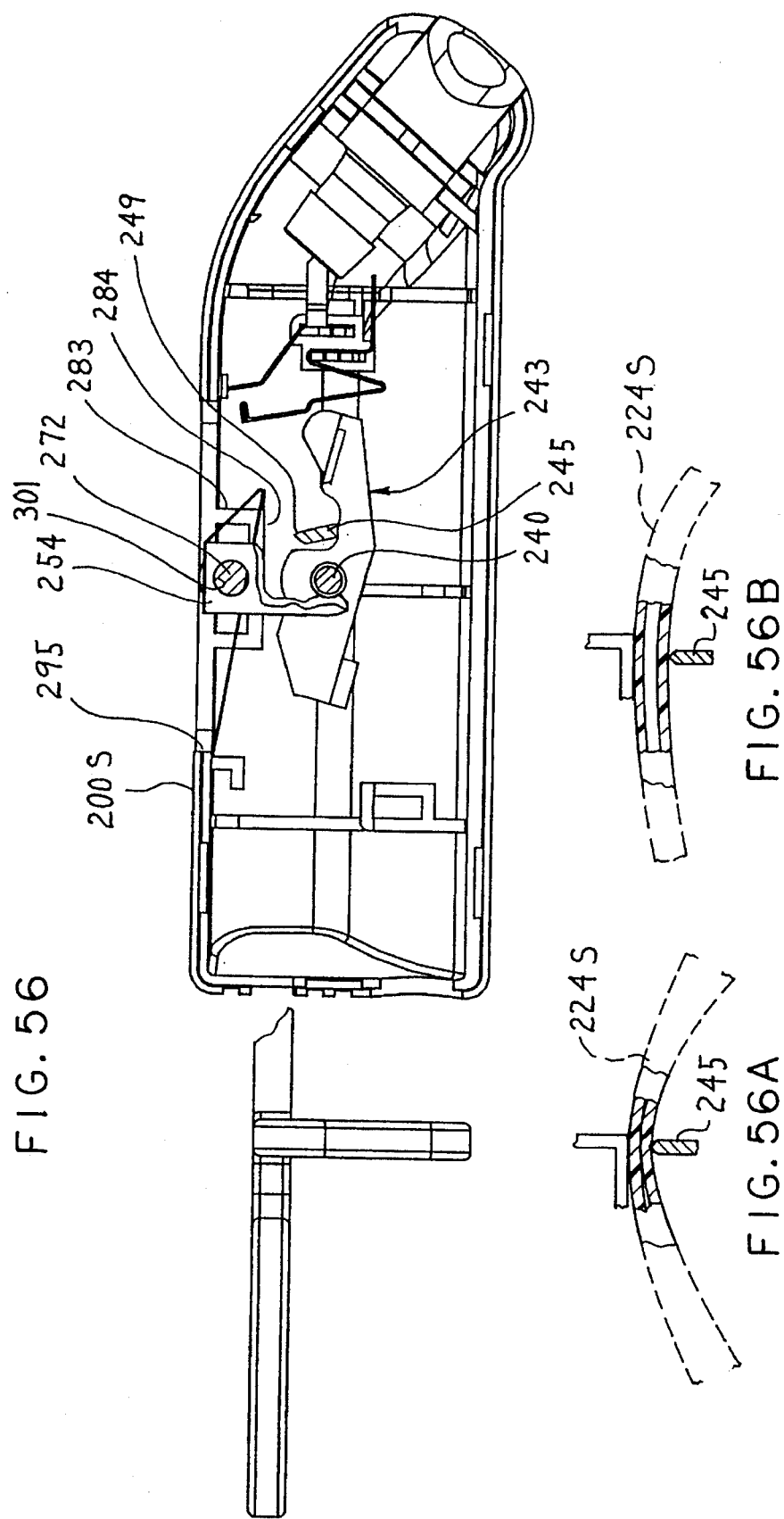
FIG. 56 is a view similar to FIG. 55 but with the rocker removed and portions of the U-spring and suction pinch lever removed to better show the suction tube pinch blade opposing the corresponding anvil surface.

The recess 294 of the rocker 290 receives upwardly thereinto the upper portion of the U-shaped part 253 of the U-spring 252, the top of the U-shaped part 253 being spaced below the top of the recess 294 in the rocker. The upper (anvil) shaft 272 (FIGS. 29 and 57) extends laterally through holes 300 in the sides 292 (FIG. 50) of the rocker 290. The anvil shaft 272 also extends through aligned holes 301 in the upper parts of the U-spring legs 254 (FIG. 56). As a result, the U-spring 272 is substantially fixed in place with respect to the shell 200 by passage of the upper and lower shafts 272 and 240 therethrough and the rocker 290 (FIG. 57) is pivoted on the anvil shaft 272 for rocking forwardly and rearwardly (clockwise or counterclockwise in the drawing) about the anvil shaft 272.

As seen in FIG. 57, the forwardly and upwardly angled front end portion 258 of the U-spring 252 lies within the downward opening recess 294 of the rocker 290 and at its forward extremity (left extremity in FIG. 57) is fixed to the front wall 293 of the rocker 292 by any convenient means, such as by being molded integrally with the rocker 290. The U-spring 252 is arranged to resiliently urge the rocker 290 to its central, horizontal position shown in FIG. 57 and to resiliently resist, but permit, forward and rearward (in FIG. 57 counterclockwise and clockwise) rocking of the rocker 290 by the user.

The rocker 290 is pivotable forward (counterclockwise in FIG. 57) to push the bottom edge of its front wall 293 down against irrigation lever front tab 247, correspondingly counterclockwise rotate the irrigation pinch lever 242, cause its pinch blade 245 to drop away from the corresponding irrigation hose 224I, and thus open the irrigation hose 224I, as in the transition from FIG. 53A to FIG. 53B. Alternately, the rocker 290 is pivotable rearward (clockwise in FIG. 57) to push the bottom edge of the rear wall 293 of the rocker 290 downward (clockwise) against the rear tab 247 of the suction pinch lever 243, correspondingly pivot same clockwise, drop its pinch blade 245 away from the corresponding suction hose 224S, and thus open the suction hose 224S, as in the transition from FIG. 56A to FIG. 56B.

Figure 48:
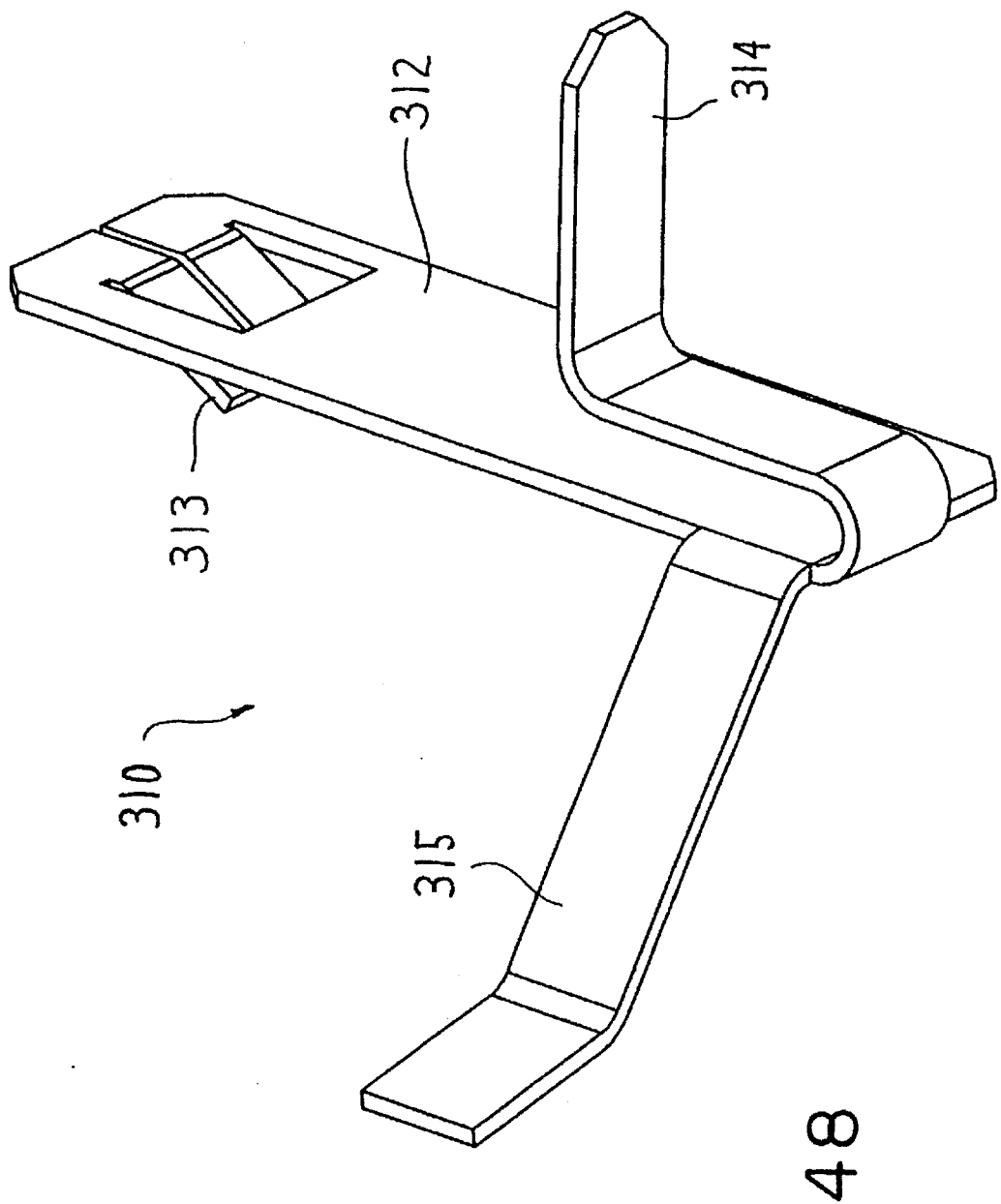
Figure 49:
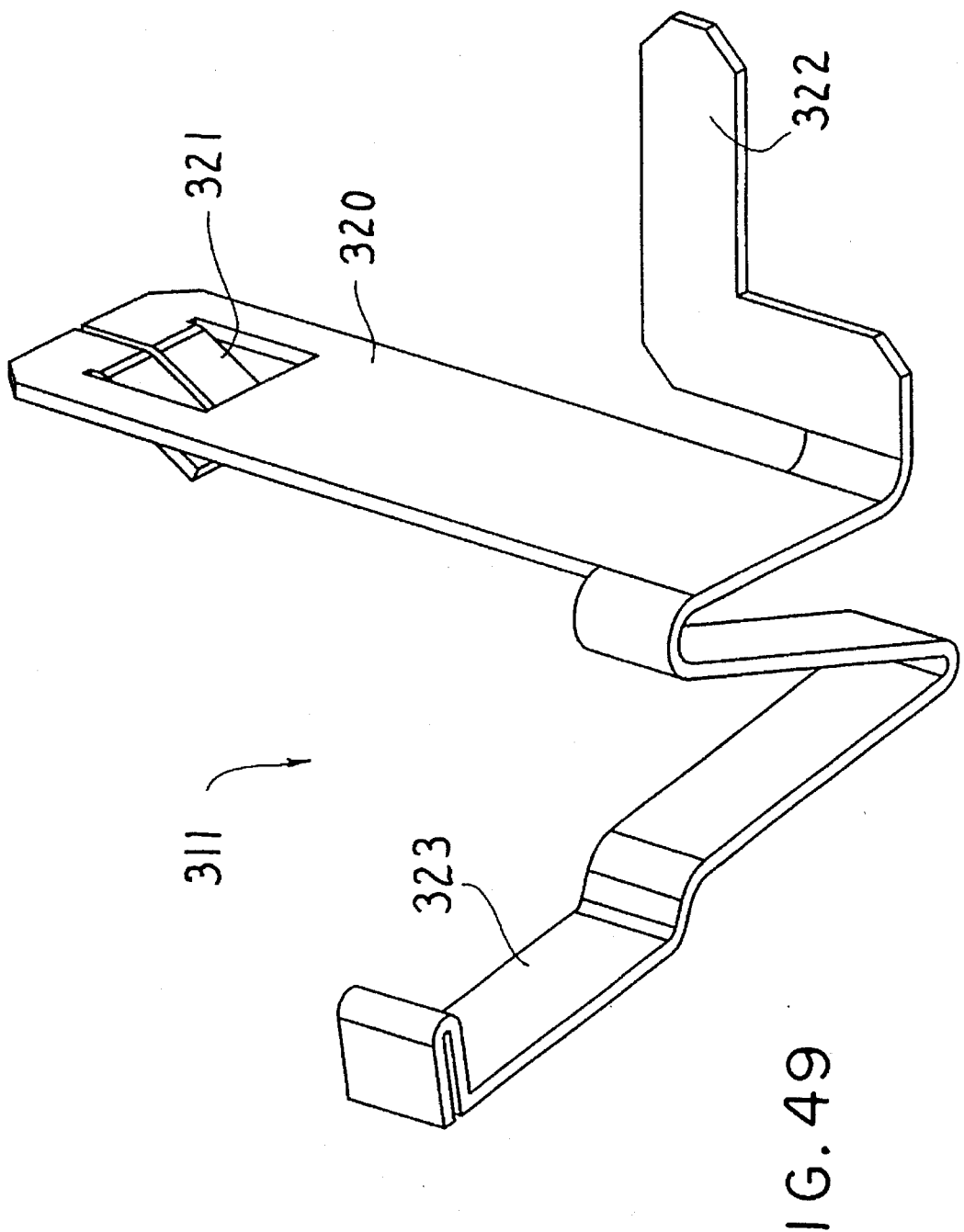
Figure 51:
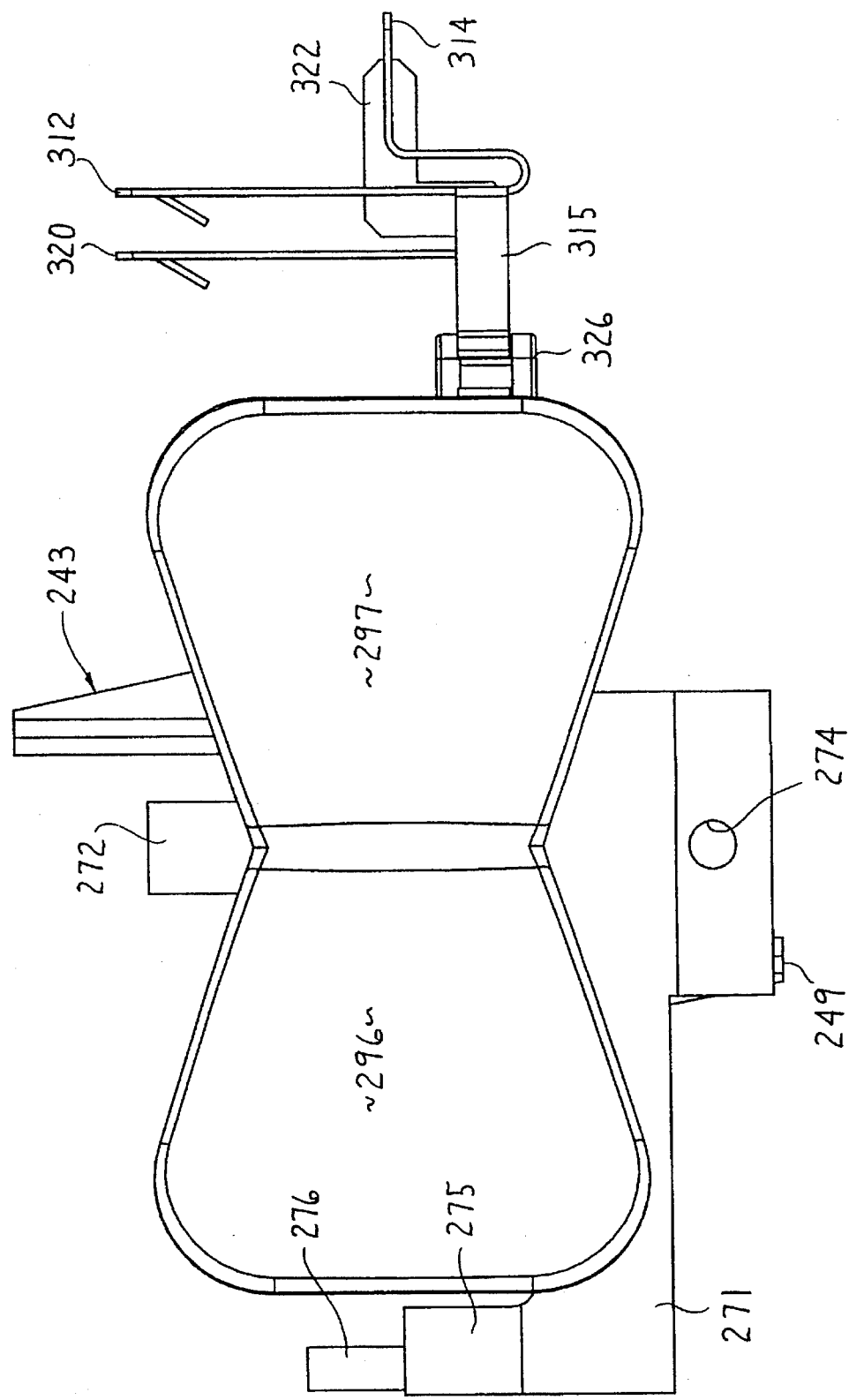
FIG. 51 is an enlarged top view of the FIG. 50 subassembly.

In the preferred embodiment shown, the electrical switch SW of the handpiece 26 is formed by a switch spring 310 and a Z-spring 311, seen in FIGS. 48 and 49 respectively. Both are formed of resiliently deflectable, electrically conductive, sheet metal. The switch spring 310 comprises a base plate 312 having a free end provided with gripper tabs 313 reflexly bent, a generally L profile female electric terminal 314 and a switch contact arm 315. Similarly, the Z-spring 311 (FIG. 49) comprises a base plate 320 whose free end is provided with gripper tabs 321, a generally L-shaped planar electric terminal 322, and a generally Z-shaped switch contact 323. The half shell 200S (FIGS. 37 and 38), to the rear of the tubular boss 241, comprises rear and front lateral recesses 325 and 324 respectively which open toward the opposite half shell 200I and are shaped to receive the gripper tab equipped, free end portions of the base plates 312 and 320 of the switch spring 310 and Z-spring 311, respectively. The switch spring and Z-spring are oriented so that their electric terminals 314 and 322 extend rearwardly (FIG. 57) and so that their switch contacts 315 and 323 respectively extend upwardly and forwardly. The top of the switch contact 323 is normally spaced slightly in front of the top portion of the switch contact 315. See also FIGS. 51 and 52.

Figure 59:
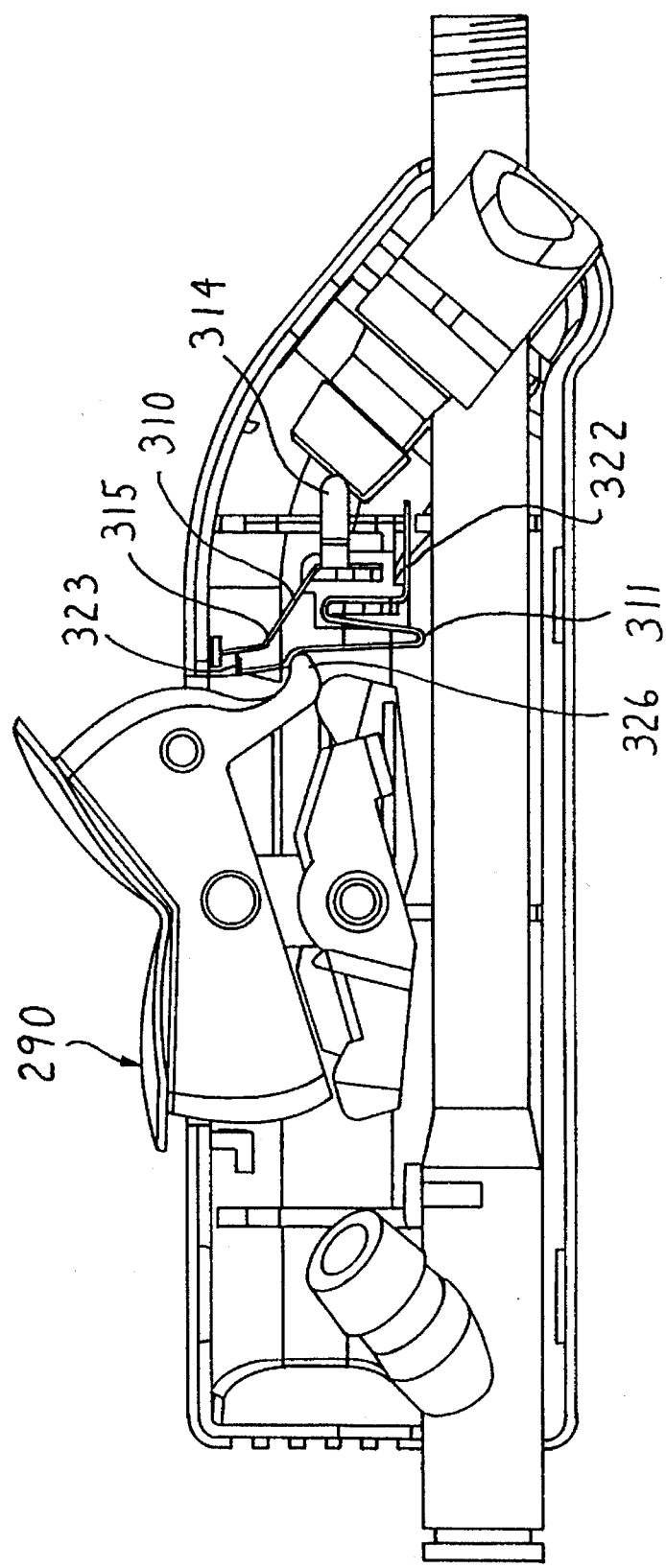
FIG. 59 is a view similar to FIG. 54 but with the guard pin entirely omitted and the rocker rocked forward in its irrigation tube open position (corresponding to FIG. 53B) and the switch contacts 323 and 315 engaged to close the battery/motor circuit and energize the motor for pumping irrigation liquid to the handpiece.

Fixed low on the rear of the rocker 290 and extending slightly rearward therefrom is a preferably integral switch actuator foot 326 (FIG. 53) arranged so that forward (counterclockwise) tilting of the rocker 290 not only opens the irrigation tube 224 by dropping the pinch blade 245 (in the transition from FIG. 53A to FIG. 53B), but also pivots the foot 326 (FIG. 59) upward and rearward, to push the switch contact 323 of the Z spring 311 rearwardly into electrical contact with the switch contact 315 of the switch spring 310. This closes the switch SW constituted by contacts 315 and 323, and, through their terminals 314 and 322, closes the electrical circuit (FIG. 22) through the motor M and array of batteries B to energize the motor and force irrigation liquid through the flexible irrigation hose 224I and then forwardly through the tip TP to a surgical site.

Figure 60:
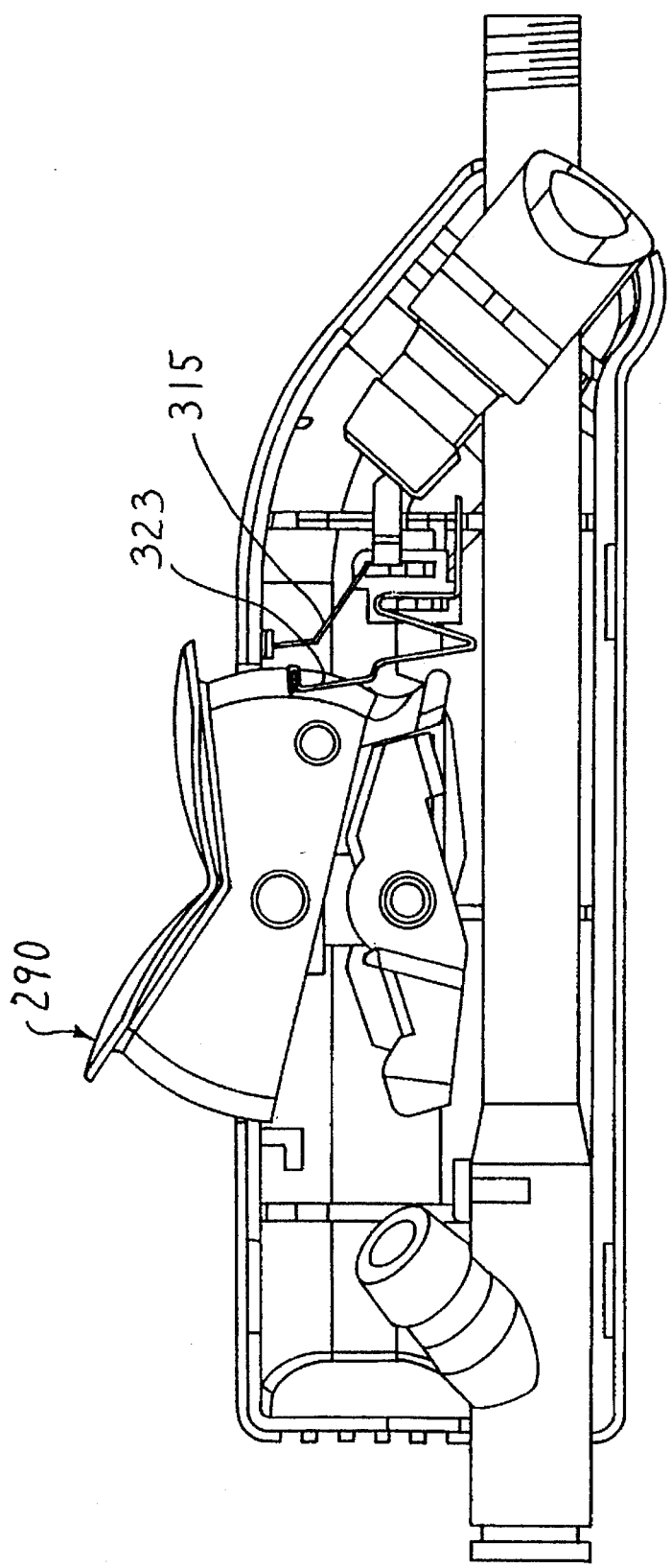
FIG. 60 is a view similar to FIG. 59 but with the rocker rocked backward to open the suction tube as schematically indicated in FIG. 56B.

On the other hand, rocking the rocker 290 rearward (clockwise in FIGS. 56 and 60) drops the pinch blade 245 of the suction pinch lever 243 to open the suction tube 224 (in the transition from FIG. 56A to 56B) to allow suction flow from the tip back to a suction source SS.

Note that only one of the pinchable hoses 224I and 224S can be opened at a time. Note also that opening of the irrigation hose 224I is automatically and positively correlated with closure of the switch SW, so as to begin pumping liquid forward through the open irrigation tube 224I.

To avoid closure of the switch SW (and resulting energization of the motor M, wear on the parts and depletion of the batteries), after the handpiece is assembled and prior to packaging for shipping, a guard pin 330 (FIG. 29) has its square cross-section, elongate shank 331 inserted rearwardly through a hole 332 in front wall 333 of the shell (FIGS. 27–29). The guard pin shank 331 (FIG. 58) extends through the front wall hole 332 rearward into the shell 200 snugly under the front and rear walls 293 of the rocker 290 to positively prevent pivoting of the rocker 290 and thereby preventing closure of the electric switch contacts 315 and 323. In addition, the guard pin shank 331 pushes downward, under their normal hose clamping positions, the tabs 247 of both pinch levers 242 and 243, so as to hold open and thus unstressed the hoses 224I and 224S during shipping and storage. FIGS. 53–58 show the parts in this storage position, with the guard pin shank 331 in solid line in FIG. 58 and in dotted line (to better show parts behind it in the drawings) in FIGS. 53–57. A shield 335 depends from the shank 331 near the ring 334 to partly cover and protect, during storage and shipping, the open front end of the conduit 210.

When the apparatus is ready for use, the guard pin 330 is withdrawn from the handpiece by forward pull on a finger ring 334 (FIG. 29) fixed on the front end of the shank 331.

Except for the springy conductive metal spring elements 252, 261, 310 and 311, and the resiliently pinchable hoses 224I and 224S, the remaining primary parts of the handpiece are formed of a suitable rigid material, by any convenient means, such as molding of a rigid plastics material.

While the operation of the disclosed apparatus will be clear from the above description, same may, for convenience, be briefly summarized as follows. To operate the disclosed apparatus, the inlet connector 12 of the pumping unit 11 is inserted in the corresponding fitting of an irrigation liquid supply (e.g. bag) IL and the pumping unit 11 is supported therebelow by means above discussed. The guard pin 330 is pulled from the handpiece 26. The tip TP of the handpiece 26 is inserted into a surgical site SU in a patient, e.g. through a cannula CA previously inserted thereinto.

Rocking the rocker 290 forward to its FIG. 1 position opens the irrigation hose 224I (FIG. 29) and closes the contacts of the switch SW (FIG. 22), energizing the motor and rotating the pump rotor 117 (FIG. 6). Insertion of the pumping unit inlet connector 12 directly into the irrigation liquid bag 14 has substantially instantaneously primed the pumping chamber with irrigation liquid so that rotation of the pump rotor 117 substantially instantaneously pumps irrigation liquid under pressure through the tube 23 (FIG. 1) through the handpiece 26, namely through the adapter block 225 (FIG. 42), hose 224I, conduit 210 and tip TP to the surgical site SU. On the other hand, rocking the rocker 290 rearward (to its FIG. 60 position) closes the hose 224I and opens the hose 224S for suctioning debris from the surgical site through the tip TP, conduit 210, open suction hose 224S, adapter 225 and suction hose 33 to a conventional suction source SS. Release of the rocker 290 causes it to resiliently center itself in its neutral FIG. 27 position, in which both the suction and irrigation hoses 224S and 224I respectively are clamped closed by their respective pinch levers 243 and 242.

The disclosed suction irrigation system 10 is totally disposable and manufacturable at relatively low cost. Upon insertion of the inlet flow connector 12 into the irrigation liquid source IL, and pulling out of the guard pin 330, the system 10 is ready for immediate use. The system provides a high flow rate of irrigation liquid (higher than usual for a disposable system). The flow rate is steady so as not to make tissue jump at the surgical site, as might a pulsed irrigation system. Location of motor, pump and batteries remotely from the handpiece, adjacent the irrigation liquid source IL, not only provides for substantially instantaneous priming of the pump but also permits a compact, very lightweight, and hence readily maneuverable handpiece 26.

Figure 1A:
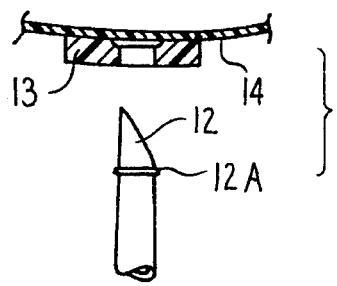
FIG. 1A is an enlarged fragmentary cross-sectional view of the bag fitting and pumping unit liquid inlet connector of FIG. 1.

In one unit built according to the invention, the connector 13 (FIGS. 1 and 1A) on the liquid supply container 14 was a conventional luer female fitting. The liquid inlet connector 12 was provided with an annular rib 12A (FIGS. 1, 2 and 4–6) adjacent its upper end to snapfit into the bag fitting 13 forcibly enough to support the weight of the pumping unit 11 (and its trailing hose 23 and cable 27) pendently from the container 14, yet allow the pumping unit 11 to be intentionally disconnected from the container 14 by pulling same apart more forcibly. Thus, the pumping unit 11 with its trailing hose 23 and cable 27 can be entirely supported pendently from the liquid supply container 14 by connection of its hollow spike 12 to the container fitting 13, or can instead be supported by separate means, exemplified by the bracket 18 of FIG. 1.

Although a particular preferred embodiment of the invention has been disclosed in detail for illustrative purposes, it will be recognized that variations or modifications of the disclosed apparatus, including the rearrangement of parts, lie within the scope of the present invention.

The embodiments of the invention in which an exclusive property or privilege is claimed are defined as follows:

1. A surgical irrigation system suitable for endoscopic and other surgical procedures, comprising:

a hand held handpiece having a forward protruding hollow tip for supplying irrigation liquid to a surgical site, hand actuable control means for controlling irrigation liquid flow to said tip, and an irrigation liquid inlet;

an irrigation liquid supply unit connected to said inlet, said hand actuable control means on said handpiece comprising a hand actuable rocker member and an irrigation rocking lever responsive to movement of said hand actuable rocker member for opening and closing irrigation liquid flow through an irrigation liquid path in said handpiece from said inlet to said tip, said handpiece including a suction path therein for connection to an external suction source and connected to said tip, said control means including a suction rocking lever responsive to movement of said rocker member for closing and opening suction flow through said suction path through said handpiece, said rocker member having a first actuated position which simultaneously opens said irrigation liquid flow through said handpiece and closes said suction path, said rocker member having a second actuated position which simultaneously closes said irrigation liquid flow and opens said suction path through said handpiece, said irrigation liquid and suction paths through said handpiece comprising respective flexible pinchably closeable hoses, fixed anvil means backing said hoses, said irrigation rocking lever and suction rocking lever having respective pinch elements thereon and spring means urging said rocking levers to a rest position pinching closed said irrigation liquid hose and suction hose.

2. The apparatus of claim 1 in which said handpiece includes a Y-shaped connection open to said tip and having a pair of ports connected respectively to said irrigation liquid path and suction path in said handpiece such that alternative opening of said irrigation and suction paths uses the same tip to apply irrigation liquid and suction alternatively to a surgical site.

3. The apparatus of claim 1 in which said handpiece includes a straight conduit open at both ends of said handpiece for forwarding an auxiliary tool therethrough to a surgical site, a Y-shaped connection to said conduit near said tip, pinchable irrigation and suction hoses running forward in said handpiece to a Y-shaped connection, such that said conduit handles irrigation liquid, suction, and auxiliary tool connection to a surgical site.

4. A surgical irrigation system suitable for endoscopic and other surgical procedures, comprising:

a hand held handpiece for supplying irrigation liquid to a surgical site;

a self contained pumping unit locatable adjacent a source of irrigation liquid and remote from said handpiece, said pumping unit comprising a housing containing an outlet for irrigation liquid, a pumping member for pumping irrigation liquid through said outlet, a motor for driving said pumping member, and electric battery means for energizing said motor;

an elongate tube for connecting said pumping outlet to said handpiece for supplying pumped irrigation liquid to said handpiece, said pumping unit housing comprising an open topped cup and a generally radially extending deck overlying the open top of the cup, said motor having a shaft protruding up through a hole in the deck and facing into a pumping chamber defined between said deck and an overlying cover, a cable running from said pumping unit to said handpiece along a cable passage through said cover and locator and the bottom of said cup, for connecting said motor and battery means to said cable, said handpiece including a switch connected to said cable for energizing said motor from said battery means upon actuation of said switch.

5. The apparatus of claim 4 in which said irrigation liquid tube and extend in close side-by-side relation from said cover, said pumping outlet being on said cover.

6. A surgical irrigation system suitable for endoscopic and other surgical procedures, comprising:

a hand held handpiece having a forward protruding hollow tip for supplying irrigation liquid to a Surgical site, hand actuable control means for controlling irrigation liquid flow to said tip, and an irrigation liquid inlet;

an irrigation liquid supply unit connected to said inlet, said irrigation liquid supply unit comprising (1) a liquid pumping member and (2) a motor energizable for driving and pumping and (3) an electric source, said hand actuable control means on said handpiece Comprising a switch and a hand actuable member and valve means responsive to movement of said hand actuable member for opening irrigation liquid flow through an irrigation liquid path in said handpiece from said inlet to said tip, means connecting said control member to said switch and valve means for substantially simultaneously opening said valve means to flow irrigation liquid through said handpiece and energizing said motor by current from said electric source, in which said handpiece includes a suction path therein for connection to an external suction source and connected to said tip, said control means including means for opening and closing said suction path through said handpiece, said control means comprising a rocker member having a first actuated position which (1) opens said irrigation liquid flow through said handpiece and (2) energizes said motor and (3) closes said suction path, said rocker member having a second actuated position which closes said irrigation liquid flow and (2) shuts off said motor and (3) opens said suction path through said handpiece.

7. The apparatus of claim 6 in which said rocker member has a neutral position blocking suction flow and irrigation flow in the handpiece and maintaining said motor off.

8. A surgical irrigation system suitable for endoscopic and other surgical procedures, comprising:
 a hand held handpiece for supplying irrigation liquid to a surgical site;
 a self contained pumping unit locatable adjacent a source of irrigation liquid and remote from said handpiece, said pumping unit comprising a housing containing an outlet for irrigation liquid a pumping member for pumping irrigation liquid through said outlet, a motor for driving said pumping member, and electric battery means for energizing said motor;
 an elongate tube for connecting said pumping outlet to said handpiece for supplying pumped irrigation liquid to said handpiece, said pumping unit housing comprising an open topped cup and a locator coaxially received in the open top of said cup and a cover closing the top of said locator, said locator comprising a generally radially extending deck overlying the open top of the cup and a column coaxially depending from said deck into said cup, said column having a central recess for receiving said motor, said motor having a shaft protruding up through a hole in the deck and facing into a pumping chamber defined between said deck and said cover.

9. The apparatus of claim 8 in which said column includes generally axially extending radially outward reaching fins circumferentially spaced by generally axially extending, radially outwardly opening grooves, said grooves and fins surrounding said motor recess, said battery means comprising plural batteries, means for locating said batteries in said grooves between said fins, in a circumferential array of batteries surrounding said motor recess.

10. The apparatus of claim 9 including electric contact means aligned with said grooves adjacent the top and bottom of said grooves, an electric contact of one said groove electrically connecting to a corresponding contact in the next groove for connecting said batteries electrically, and electric connections through the bottom of said cup for interconnecting said batteries and motor.

11. The apparatus of claim 8 including an impeller between said deck and said cover and fixed for rotation with said motor shaft, said cover and deck defining therebetween a pumping chamber, a liquid inlet fitting at the top of said cover for connection to a conventional irrigation liquid supply, and an outlet for pumped irrigation liquid through the side of said cover, said tube running from said cover outlet to said handpiece for supplying irrigation liquid in a pumped manner from said pumping chamber to said handpiece.

12. The apparatus of claim 8 in which said deck has circumferentially spaced slots adjacent the periphery thereof, said cover and cup having circumferentially spaced tabs snap fit receivable in corresponding ones of said slots in said deck for fixing said cup and cover to said locator.

13. The apparatus of claim 8 in which said deck has an upstanding, substantially cylindrical plug coaxial with said motor shaft and through which said motor shaft extends upward into said pumping chamber, said cover having a dome forming said pumping chamber, said dome having a recess extending down from said chamber and closely and sealingly receiving said plug, said cover having a radially outward flange at the bottom of said recess for closely overlying said deck and fixedly attaching thereto.

14. An endoscopic surgical irrigation system, comprising:
 a handpiece for directing irrigation liquid to a surgical site;
 a pumping unit locatable remotely from the handpiece and surgical site, an elongate irrigation liquid tube connecting said pumping unit to said handpiece for delivery of pumped irrigation liquid from said pumping unit to said handpiece, said pumping unit comprising a motor, a pumping member connected to said motor for pumping irrigation liquid into said elongate tube and through said elongate tube to said handpiece, means enclosing a pumping chamber occupied by said pumping member and having an outlet connected to said elongate tube, said pumping chamber enclosing means further including an elongate, hollow, generally tubular spike having means for (1) sealingly inserting into an outlet fitting of an irrigation liquid supply container, (2) receiving irrigation liquid from said liquid supply container and directing irrigation liquid into said pumping chamber, (3) fixing said pumping chamber enclosing means to an irrigation liquid supply container, (4) independently supporting said pumping unit from an irrigation liquid supply container and (5) gravitationally and substantially instantaneously priming said pumping chamber upon connection to an irrigation liquid supply container.

15. The apparatus of claim 14 in which a distal portion of said hollow spike includes a radially outwardly extending protrusion on said hollow spike for insertion into and capture by a fitting on an irrigation liquid supply container.

16. The apparatus of claim 15 including a conventional irrigation liquid supply container having a female fitting for snapfit reception of at least the distal portion of said hollow spike on said pumping unit, said radially extending protrusion comprising an annular rib fixed on the outside of said hollow spike for axial snap fit reception in said fitting of said irrigation liquid supply container.

17. A surgical irrigation system suitable for endoscopic and other surgical procedures, comprising:
 a hand held handpiece having a forward protruding hollow tip for supplying irrigation liquid to a surgical site, hand actuable control means for controlling irrigation liquid flow to said tip, and an irrigation liquid inlet;
 a liquid supply unit locatable remotely from said handpiece;
 a tube for connecting said liquid supply unit to said handpiece irrigation liquid inlet for supplying irrigation liquid to said handpiece, said remote liquid supply unit comprising an electric powered means actuable to increase the momentum of liquid flow from said liquid supply unit through said tube to said handpiece, said hand actuable control means of said handpiece comprising a\switch means actuable to control said actuation of said remote liquid supply unit and including an elongate remote control line extending along said irrigation liquid tube between said handpiece and remote pumping unit for operatively connecting said switch means to said electric powered means of said remote liquid supply means for remotely actuating same, in which said handpiece includes a suction path therein for connection to an external suction source and connected to said tip, said control means including means for opening and closing said suction path through said handpiece.

18. The apparatus of claim 17 in which liquid supply unit includes a motor and a pumping member driven thereby for pumping irrigation liquid through said tube to said handpiece, said control means comprising a rocker member having a neutral position blocking suction flow and irrigation flow in the handpiece and maintaining said motor off, said rocker member having a first actuated position for opening said irrigation liquid flow through said handpiece while energizing said motor, said rocker member having a second actuated position for opening said suction path through said handpiece.

\* \* \* \* \*

UNITED STATES PATENT AND TRADEMARK OFFICE
CERTIFICATE OF CORRECTION

PATENT NO. : 5,484,402
DATED : January 16, 1996
INVENTOR(S) : Heber SARAVIA et al It is certified that error appears in the above-indentified patent and that said Letters Patent is hereby corrected as shown below:

Column 14, line 39; before "extend" insert ---cable---.

Column 15, line 16; change "liquid" to ---liquid,---.

Signed and Sealed this

Tenth Day of September, 1996

Attest:

BRUCE LEHMAN

*Attesting Officer*   *Commissioner of Patents and Trademarks*